US008318741B2

(12) United States Patent
Chiou

(10) Patent No.: US 8,318,741 B2
(45) Date of Patent: *Nov. 27, 2012

(54) THERAPEUTIC COMPOSITIONS AND METHODS

(75) Inventor: George C. Chiou, College Station, TX (US)

(73) Assignee: The Texas A & M University System, College Station, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/440,851

(22) Filed: Apr. 5, 2012

(65) Prior Publication Data

US 2012/0196868 A1 Aug. 2, 2012

Related U.S. Application Data

(60) Continuation of application No. 13/304,088, filed on Nov. 23, 2011, which is a division of application No. 11/416,773, filed on May 3, 2006, now Pat. No. 8,088,773, application No. 13/440,851, which is a continuation of application No. 13/304,116, filed on Nov. 23, 2011, which is a division of application No. 11/416,773, filed on May 3, 2006, now Pat. No. 8,088,773.

(60) Provisional application No. 60/680,998, filed on May 12, 2005, provisional application No. 60/776,426, filed on Feb. 24, 2006.

(51) Int. Cl.
*A61K 31/50* (2006.01)
(52) U.S. Cl. ........................... 514/248; 514/912
(58) Field of Classification Search .................. 514/248, 514/912
See application file for complete search history.

(56) References Cited

U.S. PATENT DOCUMENTS

| 4,055,645 A | 10/1977 | Scriabine |
| 4,865,599 A | 9/1989 | Chiou et al. |
| 4,963,527 A | 10/1990 | Bombardelli et al. |
| 5,252,607 A | 10/1993 | Chiou |
| 5,422,116 A | 6/1995 | Yen et al. |
| 5,459,133 A | 10/1995 | Neufeld |
| 5,500,230 A | 3/1996 | Nathanson |
| 5,596,011 A | 1/1997 | Repine et al. |
| 5,698,155 A | 12/1997 | Grosswald et al. |
| 6,028,099 A | 2/2000 | DeJuan, Jr. |
| 6,066,675 A | 5/2000 | Wen et al. |
| 6,294,544 B1 | 9/2001 | Araie et al. |

(Continued)

FOREIGN PATENT DOCUMENTS

EP        0265042 A     4/1988

(Continued)

OTHER PUBLICATIONS

Meszaros, "Dry AMD treatments promising", Opthalmology Times, vol. 36, No. 8, 2 pgs., Apr. 15, 2011.

(Continued)

*Primary Examiner* — Sreeni Padmanabhan
*Assistant Examiner* — Gigi Huang
(74) *Attorney, Agent, or Firm* — Judy M. Mohr; Jacqueline F. Mahoney; McDermott Will & Emery LLP

(57) ABSTRACT

The present invention relates in general to therapeutic compositions and methods of use. In preferred embodiments, the invention relates to the field of eye health. In some embodiments, the invention relates to the prevention and treatment of macular degeneration by administering compounds disclosed herein. In some embodiments, the invention relates to compositions and methods of improving vision.

6 Claims, 20 Drawing Sheets

U.S. PATENT DOCUMENTS

| | | | |
|---|---|---|---|
| 6,313,155 | B1 | 11/2001 | Sponsel |
| 6,451,799 | B1 | 9/2002 | Ogawa et al. |
| 6,692,759 | B1 | 2/2004 | Wong et al. |
| 2002/0119974 | A1 | 8/2002 | Laties |
| 2003/0171375 | A1 | 9/2003 | Brazzel |
| 2004/0214215 | A1 | 10/2004 | Yu et al. |
| 2005/0059744 | A1 | 3/2005 | Donello et al. |
| 2006/0024365 | A1 | 2/2006 | Vaya et al. |
| 2008/0300292 | A1 | 12/2008 | Letts et al. |

FOREIGN PATENT DOCUMENTS

| | | |
|---|---|---|
| JP | 2004-250347 A | 9/2004 |
| WO | WO 98/10758 A1 | 3/1998 |
| WO | WO 01/10406 A2 | 2/2001 |
| WO | WO 2004/042353 A2 | 5/2004 |

OTHER PUBLICATIONS

Beauregard et al., "Effects of nitric oxide doners and nitric oxide synthase substrates on ciliary muscle contracted by carbachol and endothelin for possible use in myopia prevention", J. Ocular Pharm. Ther., vol. 17, No. 1, 3 pgs. (2004) *Abstract Only*, printed from http://www.liebertonline.com/doi/abs/10.1089/108076801750125577 on May 29, 2010.

Berge et al., "Pharmaceutical salts", J. Pharm. Sci., vol. 66, No. 1, pp. 1-19 (1977).

Chiou et al., "Ocular and cardiovascular pharmacology of tetramethylpyrazine isolated from *Ligusticum wallichii* franch", Acta Pharmacologica Sinica, vol. 12, No. 2, pp. 99-104 (1991).

Database WPI week 200138, Thomson Scienctific, London, GB; AN 2001-359955, JP2001072591A, Araya et al., Kowa Co., Ltd., Published Mar. 21, 2001 *Abstract only*.

Edwards et al., "Molecular genetics of AMD and current animal models", Angiogenesis, vol. 10, pp. 119-132 (2007).

Exner et al., "Lesser response to angiotensin-converting-enzyme inhibitor therapy in black as compared with white patients with left ventricular dysfunction", New Engl. J. Med., vol. 344, No. 18, pp. 1351-1357 (2001).

Harris et al., "The effects of dorzolamide on choroidal and retinal perfusion in non-exudative age related macular degeneration", Br J. Opthamology, vol. 87, No. 6, pp. 753-757 (2003).

International Search Report from related PCT Patent Applicaion No. PCT/US2006/017329 mailed Sep. 22, 2006, application now published as PCT Publication No. WO2006/124324 on Nov. 23, 2006.

Liu and Chiou, "Effects of Chinese herbal products on mammalian retinal functions", J. Ocular Pharm., vol. 12, No. 3, 377-386 (1996).

Macular Degeneration Partnership "What is AMD", www.AMD.org, 2pgs., Online Article printed from http://www.amd.org/what-is-amd.html on May 29, 2010.

Mayo Clinic, "Stargardt's disease: can it be treated?" MayoClinic.com, 2 pgs. (2006), Online Article printed from http://www.mayoclinic.com/print/stargardts-disease/AN00846/METHOD=print on May 27, 2008.

Miyano et al., "Pharmacological prevention of ocular inflammation induced by lens proteins", Opthalmic. Res., vol. 16 No., pp. 256-263 (1984) *Abstract Only*.

O'Shea et al., "Age related macular degeneration-terminology", The Macular Disease Society, 9 pgs., Online Article printed from http://web.archive.org/web/20031222155235/http://medweb.bham.ac.uk/easdec/eyetextbook/AMD/armd.htm on Dec. 22, 2003.

Rigas et al., "Chorioidal vascular resistance in age-related macular degeneration", Invest. Opthalmol. Vis. Sci., vol. 45, E-Abstract 31100, 3 pgs. (2004) printed from http://abstracts.iovs.org/cgi-content/abstract/45/5/3110 on Feb. 15, 2012.

Schmidt-Erfuth et al., "Management of neovascular age related macular degeneration", Prog. Ret. Eye Res. vol. 26, pp. 437-451 (2007).

Winfield, "Opthalmic products", Pharmaceutical Practice, Churchill Livingstone Edinburgh, New York, pp. 264-279 (2004).

Wright et al., "Improvement of vision in macular degeneration associated with intravenous zinc and selenium therapy: two cases", J. Nutr. Environ. Med., vol. 1, Issue 2, pp. 133-138 (1990).

Wu et al., "Neovascularization, Chloroidal", Medscape, 4 pgs. (2010) Online article printed from http://emedicine.medscape.com/1190818-overview on Nov. 17, 2010.

Xuan et al., "Improvement of ocular blood flow and retinal functions with puerarin analogs", Ocular Pharma. Thera., vol. 15, No. 3, pp. 207-216 (1999).

Xuan and Chiou, "Release of nitric Oxide bt N-Nitropyrazoles in rabbit lacrimal gland cell culture", J. Ocular Pharma. Thera., vol. 19, No. 3, pp. 265-270 (2003).

Zou et al., "Pharmacological therapy in age-related macular degeneration (AMD)", Int. J. Ophthalmology, vol. 5, No. 1, pp. 8-18 (2005).

FIGURE 12

| Compounds** | Concentration of fluorescein in the eye at 18 hr after IL-1 | | |
|---|---|---|---|
| | Control | Treated | % Inhibition |
| CK-17 | 905 ± 116 | 195±35* | 78 |
| CK-101A | 380±54 | 125±27* | 67 |
| CK-103A | 405±45 | 90±18* | 78 |
| CK-112 | 573±67 | 138±36* | 76 |
| CK-113 | 483±61 | 152±73* | 69 |
| CK-114 | 485±78 | 110±52* | 77 |
| CK-115 | 487±62 | 224±52* | 54 |
| CK-116 | 436±71 | 198±52* | 55 |
| CK-119 | 474±69 | 127±56* | 73 |
| CK-120 | 465±59 | 33±4* | 93 |
| CK-122 | 528±72 | 170±60* | 68 |

FIGURE 13

| Compounds | Dose (mg/kg,ip,t.i.d.) | Concentration of fluorescein in the eye at 18 hr after IL-1 | | |
|---|---|---|---|---|
| | | Control | Treated | % Inhibition |
| Prednisolone | 20 | 550±108 | 142±25* | 74 |
| Tetrandrine | 10 | 415±95 | 153±33* | 63 |
| Osthol | 10 | 285±46 | 60±15* | 78 |

FIGURE 14

| Compounds** | Mean Days to Failure | Net Increase |
|---|---|---|
| Control | 11.9±0.5 | — |
| Prednisolone | 14.1±1.0* | 12% |
| CK-17 | 18.2±1.2* | 53% |
| CK-101A | 18.2±0.8* | 53% |
| CK-103A | 21.0±1.0* | 76% |

FIGURE 15

| Treatment | Inflammation responses/mL | | | |
|---|---|---|---|---|
| | 0 h | 2 h | 4 h | 6 h |
| Control | 0.100±0.005 | 0.218±0.030 | 0.342±0.035 | 0.368±0.045 |
| CK-17 (3mg/kg) | 0.098±0.005[b] | 0.220±0.025[b] | 0.276±0.030[ab] | 0.298±0.070[ab] |
| CK-17 (10mg/kg) | 0.096±0.010[b] | 0.144±0.030[a] | 0.202±0.045[ab] | 0.226±0.40[ab] |
| CK-17 (30mg/kg) | 0.084±0.005[a] | 0.104±0.015[a] | 0.182±0.015[ab] | 0.198±0.025[a] |
| Aspirin (300mg/kg) | 0.074±0.005[a] | 0.116±0.030[a] | 0.122±0.030[a] | 0.184±0.015[a] |

FIGURE 16

| Treatment | 0 h | | 1 h | | 3 h | | 5 h | | 7 h | | 1 d | | 2 d | | 3 d | | 5 d | | 7 d | |
|---|---|---|---|---|---|---|---|---|---|---|---|---|---|---|---|---|---|---|---|---|
| | L | R | L | R | L | R | L | R | L | R | L | R | L | R | L | R | L | R | L | R |
| 0.1% CK-17 suspension | | | | | | | | | | | | | | | | | | | | |
| Cornea | 0 | 0 | 0 | 0 | 0 | 0 | 0 | 0 | 0 | 0 | 0 | 0 | 0 | 0 | 0 | 0 | 0 | 0 | 0 | 0 |
| Iris | 0 | 0 | 0 | 0 | 0 | 0 | 0 | 0 | 0 | 0 | 0 | 0 | 0 | 0 | 0 | 0 | 0 | 0 | 0 | 0 |
| Conjunctiva | | | | | | | | | | | | | | | | | | | | |
| a. Redness | 0 | 0 | 0 | 0.1 | 0 | 0.1 | 0.1 | 0 | 0.1 | 0 | 0 | 0.1 | 0.1 | 0.1 | 0.1 | 0 | 0.1 | 0.1 | 0.1 | 0 |
| b. Chemosis | 0 | 0 | 0 | 0 | 0 | 0 | 0 | 0 | 0 | 0 | 0 | 0 | 0 | 0 | 0 | 0 | 0 | 0 | 0 | 0 |
| c. Discharge | 0 | 0 | 0 | 0 | 0 | 0 | 0 | 0 | 0 | 0 | 0 | 0 | 0 | 0 | 0 | 0 | 0 | 0 | 0 | 0 |
| Total | 0 | 0 | 0 | 0.1 | 0 | 0.1 | 0.1 | 0 | 0.1 | 0 | 0 | 0.1 | 0.1 | 0.1 | 0.1 | 0 | 0.1 | 0.1 | 0.1 | 0 |

FIGURE 18
CK-101A
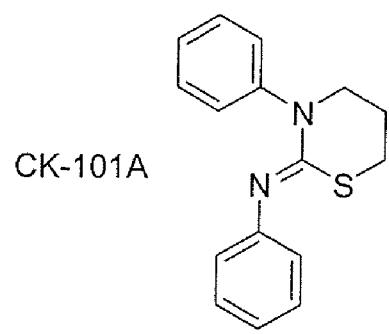
CK-103A
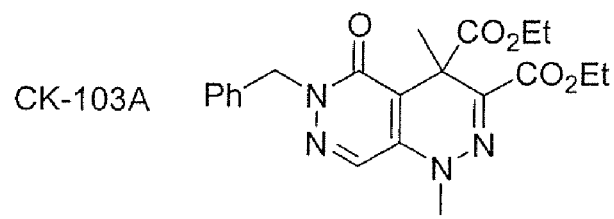
CK-103A
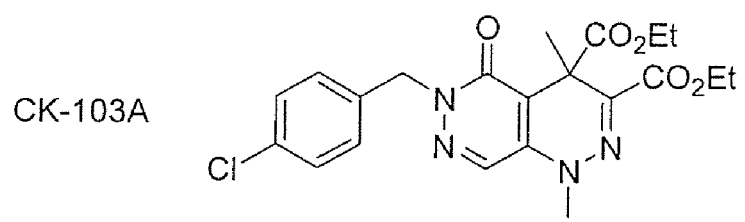
CK-120
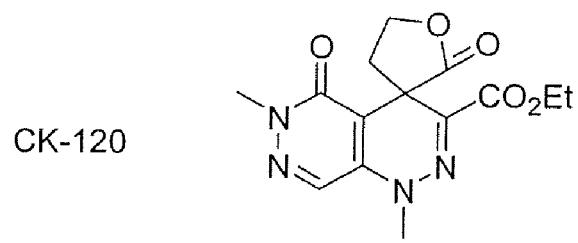
CK-122
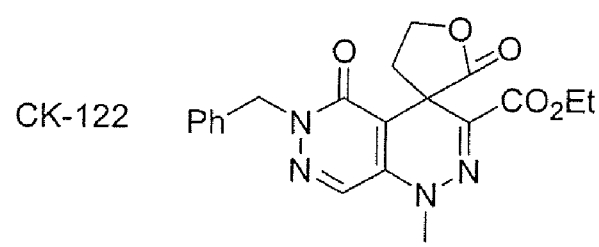

FIGURUE 19

THERAPEUTIC COMPOSITIONS AND METHODS

CROSS REFERENCE TO RELATED APPLICATIONS

This application is a continuation of U.S. patent application Ser. No. 13/304,088, filed Nov. 23, 2011, which is a divisional of U.S. patent application Ser. No. 11/416,773, filed May 3, 2006, now U.S. Pat. No. 8,088,773, which claims priority to U.S. Provisional Application No. 60/680,998, filed May 12, 2005 and U.S. Provisional Application No. 60/776, 426, filed of Feb. 24, 2006; this application is also a continuation of U.S. patent application Ser. No. 13/304,116, filed Nov. 23, 2011, which is a divisional of U.S. patent application Ser. No. 11/416,773, filed May 3, 2006, now U.S. Pat. No. 8,088,773, which claims priority to U.S. Provisional Application No. 60/680,998, filed May 12, 2005 and U.S. Provisional Application No. 60/776,426, filed of Feb. 24, 2006, all of which are incorporated by reference herein in their entirety.

TECHNICAL FIELD

The present invention relates in general to therapeutic compositions and methods of use. In preferred embodiments, the invention relates to the field of eye health. In some embodiments, the invention relates to the prevention and treatment of macular degeneration by administering compounds disclosed herein. In some embodiments, the invention relates to compositions and methods of improving vision.

BACKGROUND

Aging is a chronic process causing degeneration of cells, tissues, and organs, including choroidal blood vessels, retinal pigment epithelium cells (RPEC) and Bruch's membrane of the eye. Arteriosclerotic aging changes choroids blood vessels, particularly the macular chorio-capillaris with a decrease in total capillary membrane blood flow. As a result, retinal pigment epithelium starts to accumulate lipofuscin, alters cell shape, density, pigmentation, lysosomal activity and extracellular matrix formation. Gradually, Bruch's membrane shows thickening and decreased permeability, resulting with breakdown that allows choroidal neovascularization (CNV) to appear ultimately resulting in age-related macular degeneration and blindness. Thus, there is a need to identify agents that prevent choroidal neovascularization.

BRIEF SUMMARY

The present invention relates in general to therapeutic compositions and methods of use. In preferred embodiments, the invention relates to the field of eye health. In some embodiments, the invention relates to the prevention and treatment of macular degeneration by administering compounds disclosed herein. In some embodiments, the invention relates to compositions and methods of improving vision.

Ischemia of choroidal blood flow is one of the major causes of age-related macular degeneration (AMD). Therefore, agents have been discovered to prevent AMD formation via increasing of choroidal blood flow as measured with colored micro-sphere technique, retinal function recovery after ischemic insult, and inhibition of choroidal neovascularization in a laser treated rat model. These agents include: hypotensive agents, such as hydralazine, guanabenz, and D-timolol; flavonoids, such as apigenin, naringenin, quercetin, and flavon; and N-nitropyrazoles and C-nitro-pyrazoles, such as DN6, DN7, DN13, and DC-5. As reduction of choroidal neovascularization (CNV) serves as the major mechanism to prevent/treat AMD, agents, as demonstrated herein, prevent AMD by preventing or reducing CNV.

In some embodiments, the invention relates to methods of identifying a compound capable of treating an eye disease, preferably macular degeneration, using methods disclosed herein. Preferred methods include providing ischemic insult, measuring retinal function recovery, and correlating inhibition of neovascularization to a compound effective for preventing or treating eye diseases.

In one embodiment, the effective amount of the agent is between 0.1 and 250 mg/kg of the patient's weight, depending on the amount of active agent required and as taught herein. The agent may be adapted for oral, parenteral, intravenous, topical, intracameral or intraocular administration. In one embodiment, the agent is provided in dry form, e.g., lyophilized and may be resuspended using, e.g., saline, buffered saline and the like. The agent may be combined with a suitable carrier, e.g., an anionic, mucomimetic polymer; a gelling polysaccharide; a finely-divided drug carrier substrate; a mineral oil; a liquid petrolatum; a white petrolatum; a propylene glycol; a polyoxyethylene; a polyoxypropylene; an emulsifying wax; water and mixtures and combinations thereof.

The present invention also includes a method for treating, preventing or managing age-related macular degeneration by administering to a subject in need thereof a composition that includes an effective amount of an agent that increases choroidal blood flow. Generally, the composition may be administered after the occurrence of an acute ischemic trauma event, may be used before any symptoms are visible or detectable, during and/or after ischemic trauma.

The subject may be any mammal, e.g., the subject may be a human. The effective amount of the agent for pre-treatment, treatment or even post operative treatment (when used in conjunction with physical intervention and/or other pharmacological therapy) may be determined by measuring one or more retinal and/or choroidal functions during the recovery after an ischemic insult. Depending on the one or more agents selected for treatment, these may be provided to maximize the effectiveness of the agent, e.g., the effective amount of the agent may be between about 0.1 to about 250 mg/Kg depending on the patient's current and future needs for treatment.

In some embodiments, the invention relates to a method of treating or preventing macular degeneration comprising: 1) providing i) a subject diagnosed with or at risk for macular degeneration and ii) a composition comprising compounds disclosed herein or salt thereof and substituted and unsubstituted derivatives thereof functioning to decrease choroidal neovascularization and 2) administering said compound to said subject. In further embodiments, said eye disease is age-related macular degeneration. In further embodiments, said subject is a human. In further embodiments, said administration is topically to the eye. In further embodiments, said salt is a hydrochloride salt. In further embodiments, said composition is a liquid solution.

In some embodiments, the invention relates to a method of treating or preventing macular degeneration comprising: 1) providing i) a subject that exhibits a symptom of macular degeneration, and in further embodiments said administering causes a reduction in said symptom and ii) a composition comprising compounds disclosed herein or salt thereof and substituted and unsubstituted derivatives thereof functioning to decrease choroidal neovascularization and 2) administering said compound to said subject. In further embodiments, said eye disease is age-related macular degeneration. In further embodiments, said subject is a human. In further embodiments, said administration is topically to the eye. In further embodiments, said salt is a hydrochloride salt. In further embodiments, said composition is a liquid solution.

In some embodiments, the invention relates to a method of treating or preventing macular degeneration comprising: 1) providing i) a subject that exhibits a symptom of macular degeneration, and in further embodiments said administering causes a reduction in said symptom and ii) a composition comprising tetramethylpyrazine or salt thereof and 2) administering said compound to said subject. In further embodiments, said macular degeneration is age-related. In further embodiments, said subject is a human. In further embodiments, said administration is topically to the eye. In further embodiments, said salt is a hydrochloride salt. In further embodiments, said composition is a liquid solution.

In some embodiments, the invention relates to a method of treating or preventing macular degeneration comprising: 1) providing i) a subject diagnosed or at risk for macular degeneration and ii) a composition comprising tetramethylpyrazine or salt thereof and 2) administering said compound to said subject. In further embodiments, said macular degeneration is age-related. In further embodiments, said subject is a human. In further embodiments, said administration is topically to the eye. In further embodiments, said salt is a hydrochloride salt. In further embodiments, said composition is a liquid solution.

In some embodiments, the invention relates to a method of treating or preventing an eye disease comprising: 1) providing i) a subject and ii) a composition comprising agent or salt thereof and 2) administering said compound to said subject. In further embodiments, said eye disease is macular degeneration. In further embodiments, said subject is a human. In further embodiments, said administration is topically to the eye. In further embodiments, said salt is a hydrochloride salt. In further embodiments, said composition is a liquid solution. In further embodiments, said agent composition is greater than 50%, 55%, 60%, 65%, 70%, 75%, 80%, 85%, 90%, 95%, 98%, 99%, 99.5% or 99.9% by weight of an isomeric component. In further embodiments, the subject is diagnosed or at risk for macular degeneration. In further embodiments, said subject exhibits a symptom of macular degeneration, and in further embodiments said administering causes a reduction in said symptom In some embodiments, the invention relates to a method of treating or preventing macular degeneration comprising: 1) providing i) a subject diagnosed with or at risk for macular degeneration and ii) a composition comprising timolol or salt thereof and 2) administering said compound to said subject. In further embodiments, said macular degeneration is age-related. In further embodiments, said subject is a human. In further embodiments, said administration is topically to the eye. In further embodiments, said salt is a hydrochloride salt. In further embodiments, said composition is a liquid solution. In further embodiments, said timolol composition is greater than 50%, 55%, 60%, 65%, 70%, 75%, 80%, 85%, 90%, 95%, 98%, 99%, 99.5% or 99.9% by weight of a D-timolol component.

In some embodiments, the invention relates to a method of treating or preventing macular degeneration comprising: 1) providing i) a subject that exhibits a symptom of macular degeneration, and in further embodiments said administering causes a reduction in said symptom and ii) a composition comprising timolol or salt thereof and 2) administering said compound to said subject. In further embodiments, said macular degeneration is age-related. In further embodiments, said subject is a human. In further embodiments, said administration is topically to the eye. In further embodiments, said salt is a hydrochloride salt. In further embodiments, said composition is a liquid solution. In further embodiments, said timolol composition is greater than 50%, 55%, 60%, 65%, 70%, 75%, 80%, 85%, 90%, 95%, 98%, 99%, 99.5% or 99.9% by weight of a D-timolol component.

In some embodiments, the invention relates to a method of treating or preventing macular degeneration comprising: 1) providing i) a subject diagnosed with or at risk for macular degeneration and ii) a composition comprising a substituted or unsubstituted compound of the following formula:

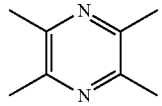

or salt thereof functioning to decrease choroidal neovascularization and 2) administering said compound to said subject.

In some embodiments, the invention relates to a method of treating or preventing macular degeneration comprising: 1) providing i) a subject that exhibits a symptom of macular degeneration, and in further embodiments said administering causes a reduction in said symptom and ii) a composition comprising a substituted or unsubstituted compound of the following formula:

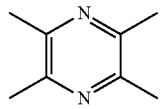

or salt thereof functioning to decrease choroidal neovascularization and 2) administering said compound to said subject.

In additional embodiments, the invention relates to a method of treating or preventing macular degeneration comprising: 1) providing i) a subject diagnosed with or at risk for macular degeneration and ii) a composition comprising hydralazine or salt thereof and 2) administering said compound to said subject. In further embodiments, said macular degeneration is age-related. In further embodiments, said subject is a human. In further embodiments, said administration is topically to the eye. In further embodiments, said salt is selected from the group consisting of a hydrochloride salt, hydrochlorothiazide salt or isosorbide dinitrate salt. In further embodiments, said composition is a liquid solution.

In additional embodiments, the invention relates to a method of treating or preventing macular degeneration comprising: 1) providing i) a subject that exhibits a symptom of macular degeneration, and in further embodiments said administering causes a reduction in said symptom and ii) a composition comprising hydralazine or salt thereof and 2) administering said compound to said subject. In further embodiments, said macular degeneration is age-related. In further embodiments, said subject is a human. In further embodiments, said administration is topically to the eye. In further embodiments, said salt is selected from the group consisting of a hydrochloride salt, hydrochlorothiazide salt or isosorbide dinitrate salt. In further embodiments, said composition is a liquid solution.

In another embodiment, the invention relates to a method of treating or preventing macular degeneration comprising: 1) providing i) a subject a subject diagnosed with or at risk for macular degeneration and ii) a composition comprising a substituted or unsubstituted compound of the following formula:

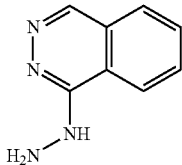

or salt thereof functioning to decrease choroidal neovascularization and 2) administering said compound to said subject.

In another embodiment, the invention relates to a method of treating or preventing macular degeneration comprising: 1) providing i) a subject a subject that exhibits a symptom of macular degeneration, and in further embodiments said administering causes a reduction in said symptom and ii) a composition comprising a substituted or unsubstituted compound of the following formula:

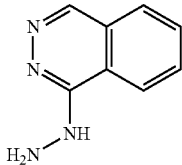

or salt thereof functioning to decrease choroidal neovascularization and 2) administering said compound to said subject.

In another embodiment, the invention relates to a method of treating or preventing macular degeneration comprising: 1) providing i) a subject diagnosed with or at risk for macular degeneration and ii) a composition comprising guanabenz or salt thereof and 2) administering said compound to said subject. In further embodiments, macular degeneration is age-related. In further embodiments, said subject is a human. In further embodiments, said administration is topically to the eye. In further embodiments, said salt is selected from the group of a hydrochloride salt and an acetate salt. In further embodiments, said composition is a liquid solution.

In another embodiment, the invention relates to a method of treating or preventing macular degeneration comprising: 1) providing i) a subject that exhibits a symptom of macular degeneration, and in further embodiments said administering causes a reduction in said symptom and ii) a composition comprising guanabenz or salt thereof and 2) administering said compound to said subject. In further embodiments, macular degeneration is age-related. In further embodiments, said subject is a human. In further embodiments, said administration is topically to the eye. In further embodiments, said salt is selected from the group of a hydrochloride salt and an acetate salt. In further embodiments, said composition is a liquid solution.

In some embodiments, the invention relates to a method of treating or preventing macular degeneration comprising: 1) providing i) a subject diagnosed with or at risk for macular degeneration and ii) a composition comprising a substituted or unsubstituted compound of the following formula:

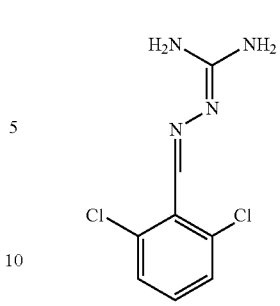

or salt thereof functioning to decrease choroidal neovascularization and 2) administering said compound to said subject.

In some embodiments, the invention relates to a method of treating or preventing macular degeneration comprising: 1) providing i) a subject that exhibits a symptom of macular degeneration, and in further embodiments said administering causes a reduction in said symptom and ii) a composition comprising a substituted or unsubstituted compound of the following formula:

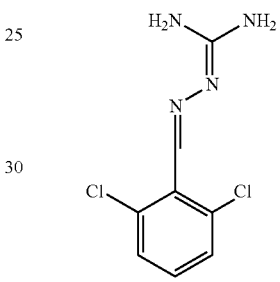

or salt thereof functioning to decrease choroidal neovascularization and 2) administering said compound to said subject.

In some embodiments, the invention relates to a method of treating or preventing macular degeneration comprising: 1) providing i) a subject a subject diagnosed with or at risk for macular degeneration and ii) a composition comprising a compound having the following structure:

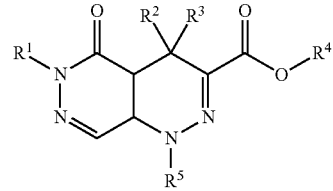

or salt thereof wherein, $R^1$ is hydrogen, alkyl, aryl, or arylalkyl; $R^2$ and $R^3$ are the same or different and, at each occurrence, independently hydrogen, alkyl, or alkylcarboxyl; $R^2$ and $R^3$ together form a five membered lactone ring; $R^4$ is hydrogen or alkyl; and $R^5$ is alkyl; and 2) administering said compound to said subject. In further embodiments, said macular degeneration is age-related. In further embodiments, said subject is a human. In further embodiments, said administration is topically to the eye. In further embodiments, said salt is a hydrochloride salt. In further embodiments, said composition is a liquid solution.

In some embodiments, the invention relates to a method of treating or preventing macular degeneration comprising: 1) providing i) a subject a subject that exhibits a symptom of macular degeneration, and in further embodiments said administering causes a reduction in said symptom and ii) a composition comprising a compound having the following structure:

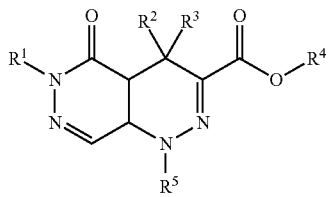

or salt thereof wherein, $R^1$ is hydrogen, alkyl, aryl, or arylalkyl; $R^2$ and $R^3$ are the same or different and, at each occurrence, independently hydrogen, alkyl, or alkylcarboxyl; $R^2$ and $R^3$ together form a five membered lactone ring; $R^4$ is hydrogen or alkyl; and $R^5$ is alkyl; and 2) administering said compound to said subject. In further embodiments, said macular degeneration is age-related. In further embodiments, said subject is a human. In further embodiments, said administration is topically to the eye. In further embodiments, said salt is a hydrochloride salt. In further embodiments, said composition is a liquid solution.

In further embodiments, the invention relates to a method of treating or preventing macular degeneration comprising: 1) providing i) a subject diagnosed with or at risk for macular degeneration and ii) a composition comprising a substituted or unsubstituted compound of the following formula:

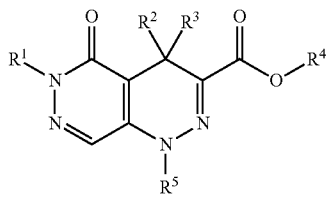

or salt thereof functioning to decrease choroidal neovascularization wherein, $R^1$ is hydrogen, alkyl, substituted alkyl, aryl, substituted aryl, arylalkyl, and substituted arylalkyl; $R^2$ and $R^3$ are the same or different and, at each occurrence, independently hydrogen, alkyl, substituted alkyl, alkylcarboxyl or substituted alkylcarboxyl; or $R^2$ and $R^3$ together and the carbon to which they are attached form a substituted or unsubstituted five membered lactone; $R^4$ is hydrogen, alkyl or substituted alkyl; and $R^5$ is hydrogen, alkyl or substituted alkyl; 2) administering said compound to said subject.

In further embodiments, the invention relates to a method of treating or preventing macular degeneration comprising: 1) providing i) a subject that exhibits a symptom of macular degeneration, and in further embodiments said administering causes a reduction in said symptom and ii) a composition comprising a substituted or unsubstituted compound of the following formula:

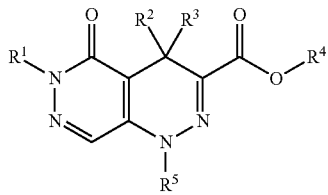

or salt thereof functioning to decrease choroidal neovascularization wherein, $R^1$ is hydrogen, alkyl, substituted alkyl, aryl, substituted aryl, arylalkyl, and substituted arylalkyl; $R^2$ and $R^3$ are the same or different and, at each occurrence, independently hydrogen, alkyl, substituted alkyl, alkylcarboxyl or substituted alkylcarboxyl; or $R^2$ and $R^3$ together and the carbon to which they are attached form a substituted or unsubstituted five membered lactone; $R^4$ is hydrogen, alkyl or substituted alkyl; and $R^5$ is hydrogen, alkyl or substituted alkyl; 2) administering said compound to said subject.

In additional embodiments, the invention relates to a method of treating or preventing macular degeneration comprising: I) providing i) a subject diagnosed with or at risk for macular degeneration and ii) a composition comprising a compound having the following structure:

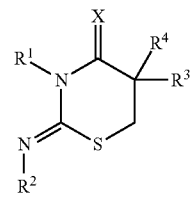

or salt thereof wherein, $R^1$ and $R^2$ are the same or different and, at each occurrence, independently hydrogen or aryl; $R^3$ and $R^4$ are the same or different and, at each occurrence, independently hydrogen, halogen, or alkyl; X is =O or two hydrogens each independently bonded to the carbon by a single bond and 2) administering said compound to said subject. In further embodiments, said macular degeneration is age-related. In further embodiments, said subject is a human. In further embodiments, said administration is topically to the eye. In further embodiments, said salt is a hydrochloride salt. In further embodiments, said composition is a liquid solution.

In additional embodiments, the invention relates to a method of treating or preventing macular degeneration comprising: 1) providing i) a subject that exhibits a symptom of macular degeneration, and in further embodiments said administering causes a reduction in said symptom and ii) a composition comprising a compound having the following structure:

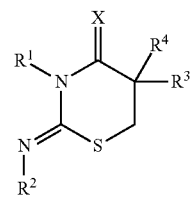

or salt thereof wherein, $R^1$ and $R^2$ are the same or different and, at each occurrence, independently hydrogen or aryl; $R^3$ and $R^4$ are the same or different and, at each occurrence, independently hydrogen, halogen, or alkyl; X is =O or two hydrogens each independently bonded to the carbon by a single bond and 2) administering said compound to said subject. In further embodiments, said macular degeneration is age-related. In further embodiments, said subject is a human. In further embodiments, said administration is topically to the eye. In further embodiments, said salt is a hydrochloride salt. In further embodiments, said composition is a liquid solution.

In some embodiments, the invention relates to a method of treating or preventing macular degeneration comprising: 1) providing i) a subject diagnosed with or at risk for macular degeneration and ii) a composition comprising a substituted or unsubstituted compound having the following structure:

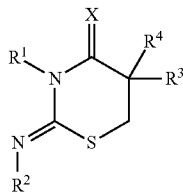

or salt thereof wherein, $R^1$ and $R^2$ are the same or different and, at each occurrence, independently hydrogen, aryl or substituted aryl; $R^3$ and $R^4$ are the same or different and, at each occurrence, independently hydrogen, halogen, alkyl or substituted alkyl; X is =O or two hydrogens each independently bonded to the carbon by a single bond; and 2) administering said compound to said subject.

In some embodiments, the invention relates to a method of treating or preventing macular degeneration comprising: 1) providing i) a subject that exhibits a symptom of macular degeneration, and in further embodiments said administering causes a reduction in said symptom and ii) a composition comprising a substituted or unsubstituted compound having the following structure:

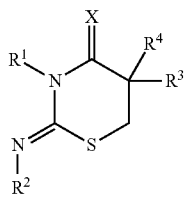

or salt thereof wherein, $R^1$ and $R^2$ are the same or different and, at each occurrence, independently hydrogen, aryl or substituted aryl; $R^3$ and $R^4$ are the same or different and, at each occurrence, independently hydrogen, halogen, alkyl or substituted alkyl; X is =O or two hydrogens each independently bonded to the carbon by a single bond; and 2) administering said compound to said subject.

In additional embodiments, the invention relates to a method of treating or preventing macular degeneration comprising: 1) providing i) a subject diagnosed with or at risk for macular degeneration and ii) a composition comprising flavon and 2) administering said compound to said subject. In further embodiments, said macular degeneration is age-related. In further embodiments, said subject is a human. In further embodiments, said administration is topically to the eye. In further embodiments, said composition is a liquid solution.

In additional embodiments, the invention relates to a method of treating or preventing macular degeneration comprising: 1) providing i) a subject that exhibits a symptom of macular degeneration, and in further embodiments said administering causes a reduction in said symptom and ii) a composition comprising flavon and 2) administering said compound to said subject. In further embodiments, said macular degeneration is age-related. In further embodiments, said subject is a human. In further embodiments, said administration is topically to the eye. In further embodiments, said composition is a liquid solution.

In some embodiments, the invention relates to a method of treating or preventing macular degeneration comprising: 1) providing i) a subject diagnosed with or at risk for macular degeneration and ii) a composition comprising a substituted or unsubstituted compound of the following formula:

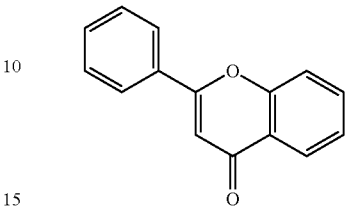

functioning to decrease choroidal neovascularization and 2) administering said compound to said subject. In further embodiments, said substituted compound is quercetin, apigenin or puerarin. In further embodiments, said subject is a human. In further embodiments, said administration is topically to the eye. In further embodiments, said composition is a liquid solution.

In some embodiments, the invention relates to a method of treating or preventing macular degeneration comprising: 1) providing i) a subject that exhibits a symptom of macular degeneration, and in further embodiments said administering causes a reduction in said symptom and ii) a composition comprising a substituted or unsubstituted compound of the following formula:

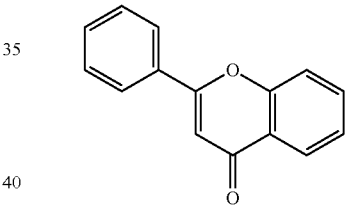

functioning to decrease choroidal neovascularization and 2) administering said compound to said subject. In further embodiments, said substituted compound is quercetin, apigenin or puerarin. In further embodiments, said subject is a human. In further embodiments, said administration is topically to the eye. In further embodiments, said composition is a liquid solution.

In additional embodiments, the invention relates to a method of treating or preventing macular degeneration comprising: 1) providing i) a subject diagnosed with or at risk for macular degeneration and a composition comprising prednisolone and salts thereof and 2) administering said compound to said subject. In further embodiments, said macular degeneration is age-related. In further embodiments, said subject is a human. In further embodiments, said administration is topically to the eye. In further embodiments, said composition is a liquid solution.

In additional embodiments, the invention relates to a method of treating or preventing macular degeneration comprising: 1) providing i) a subject that exhibits a symptom of macular degeneration, and in further embodiments said administering causes a reduction in said symptom and ii) a composition comprising prednisolone and salts thereof and 2) administering said compound to said subject. In further embodiments, said macular degeneration is age-related. In further embodiments, said subject is a human. In further embodiments, said administration is topically to the eye. In further embodiments, said composition is a liquid solution.

In some embodiments, the invention relates to a method of treating or preventing macular degeneration comprising: 1) providing i) a subject diagnosed with or at risk for macular degeneration and ii) a composition comprising a substituted or unsubstituted compound of the following formula:

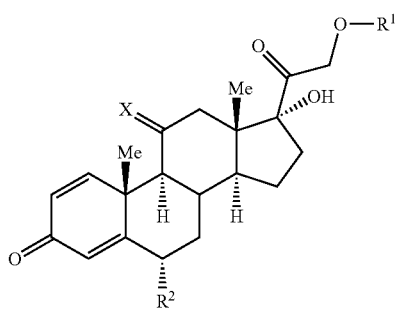

and salts thereof wherein, $R^1$ is hydrogen, phosphate, alkylcarbonyl, or succinyl and $R^2$ is hydrogen or alkyl, and X is =O or one hydrogen and one hydroxyl each independently bonded to the carbon by a single bond; functioning to decrease choroidal neovascularization and 2) administering said compound to said subject. In further embodiments, said salt is a sodium salt. In further embodiments, said compound is prednisolone, prednisolone acetate, prednisolone sodium phosphate, prednisolone tebutate, prednisone, methylprednisolone, methylprednisolone acetate, or methylprednisolone sodium succinate.

In some embodiments, the invention relates to a method of treating or preventing macular degeneration comprising: 1) providing i) a subject that exhibits a symptom of macular degeneration, and in further embodiments said administering causes a reduction in said symptom and ii) a composition comprising a substituted or unsubstituted compound of the following formula:

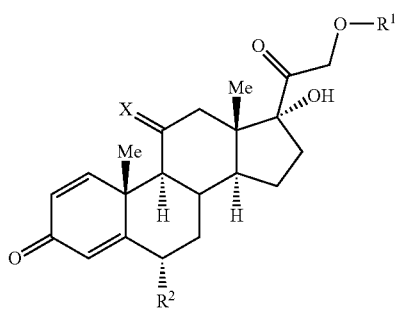

and salts thereof wherein, $R^1$ is hydrogen, phosphate, alkylcarbonyl, or succinyl and $R^2$ is hydrogen or alkyl, and X is =O or one hydrogen and one hydroxyl each independently bonded to the carbon by a single bond; functioning to decrease choroidal neovascularization and 2) administering said compound to said subject. In further embodiments, said salt is a sodium salt. In further embodiments, said compound is prednisolone, prednisolone acetate, prednisolone sodium phosphate, prednisolone tebutate, prednisone, methylprednisolone, methylprednisolone acetate, or methylprednisolone sodium succinate.

In some embodiments, the invention relates to a method of treating or preventing macular degeneration comprising: 1) providing i) a subject diagnosed with or at risk for macular degeneration and ii) a composition comprising a compound having the formula:

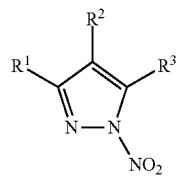

wherein $R^1$ is hydrogen, nitro, alkyl, or —(C=O)$R^4$, $R^2$ is hydrogen, nitro, alkyl or halogen, $R^3$ is hydrogen or alky, and $R^4$ is hydroxyl, —NHOMe, or

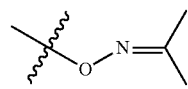

and; 2) administering said compound to said subject. In further embodiments, said subject is a human. In further embodiments, said administration is topically to the eye.

In some embodiments, the invention relates to a method of treating or preventing macular degeneration comprising: I) providing i) a subject that exhibits a symptom of macular degeneration, and in further embodiments said administering causes a reduction in said symptom and ii) a composition comprising a compound having the formula:

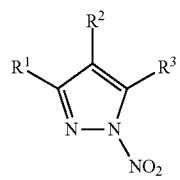

wherein $R^1$ is hydrogen, nitro, alkyl, or —(C=O)$R^4$, $R^2$ is hydrogen, nitro, alkyl or halogen, $R^3$ is hydrogen or alky, and $R^4$ is hydroxyl, —NHOMe, or

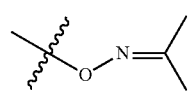

and; 2) administering said compound to said subject. In further embodiments, said subject is a human. In further embodiments, said administration is topically to the eye.

In some embodiments, the invention relates to a method of treating or preventing macular degeneration comprising: 1) providing i) a subject diagnosed with or at risk for macular degeneration and ii) a composition comprising a substituted or unsubstituted a compound having the formula:

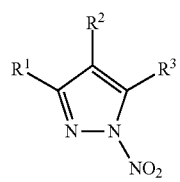

wherein $R^1$ is hydrogen, nitro, alkyl, or —(C=O)$R^4$, $R^2$ is hydrogen, nitro, alkyl or halogen, $R^3$ is hydrogen or alky, and $R^4$ is hydroxyl, —NHOMe, or

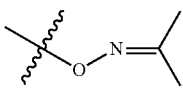

or salt thereof functioning to decrease choroidal neovascularization; and 2) administering said compound to said subject.

In some embodiments, the invention relates to a method of treating or preventing macular degeneration comprising: 1) providing i) a subject that exhibits a symptom of macular degeneration, and in further embodiments said administering causes a reduction in said symptom and ii) a composition comprising a substituted or unsubstituted a compound having the formula:

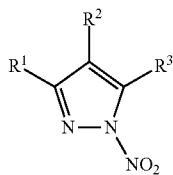

wherein $R^1$ is hydrogen, nitro, alkyl, or —(C=O)$R^4$, $R^2$ is hydrogen, nitro, alkyl or halogen, $R^3$ is hydrogen or alky, and $R^4$ is hydroxyl, —NHOMe, or

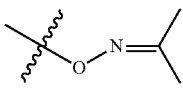

or salt thereof functioning to decrease choroidal neovascularization; and 2) administering said compound to said subject.

In some embodiments, the invention relates to a method of treating or preventing macular degeneration comprising: 1) providing i) a subject diagnosed with or at risk for macular degeneration and ii) a composition comprising a substituted or unsubstituted a compound having the formula:

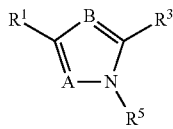

wherein $R^1$ is hydrogen, nitro, alkyl, or —(C—O)$R^4$, B is N or C—$R^2$, $R^2$ is hydrogen, nitro, alkyl or halogen, $R^3$ is hydrogen, nitro, —$CO_2$H, or alky, $R^4$ is hydroxyl, —NHOMe, or

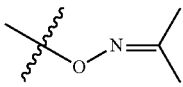

A is C—H or N, and $R^5$ is hydrogen, —$CH_2CO_2$H, or nitro. In a preferred embodiment, $R^3$ is nitro and $R^5$ is hydrogen. In another preferred embodiment, B is C—$R^2$ wherein $R^2$ is nitro and $R^5$ is hydrogen. In another preferred embodiments, $R^1$ is nitro and $R^5$ is hydrogen and $R^3$ is —$CO_2$H or salt thereof functioning to decrease choroidal neovascularization; and 2) administering said compound to said subject.

In some embodiments, the invention relates to a method of treating or preventing macular degeneration comprising: 1) providing i) a subject that exhibits a symptom of macular degeneration, and in further embodiments said administering causes a reduction in said symptom and ii) a composition comprising a substituted or unsubstituted a compound having the formula:

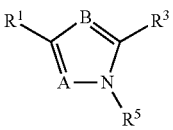

wherein $R^1$ is hydrogen, nitro, alkyl, or —(C=O)$R^4$, B is N or C—$R^2$, $R^2$ is hydrogen, nitro, alkyl or halogen, $R^3$ is hydrogen, nitro, —$CO_2$H, or alky, $R^4$ is hydroxyl, —NHOMe, or

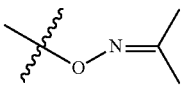

A is C—H or N, and $R^5$ is hydrogen, —$CH_2CO_2$H, or nitro. In a preferred embodiment, $R^3$ is nitro and $R^3$ is hydrogen. In another preferred embodiment, B is C—$R^2$ wherein $R^2$ is nitro and $R^5$ is hydrogen. In another preferred embodiments, $R^1$ is nitro and $R^5$ is hydrogen and $R^3$ is —$CO_2$H or salt thereof functioning to decrease choroidal neovascularization; and 2) administering said compound to said subject.

In some embodiments, the invention relates to a method of treating or preventing macular degeneration comprising: 1) providing i) a subject diagnosed with or at risk for macular degeneration and ii) a composition comprising a substituted or unsubstituted compound having the formula:

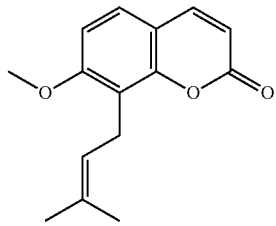

and derivatives thereof and 2) administering said compound to said subject. In further embodiments, said macular degeneration is age-related. In further embodiments, said subject is a human. In further embodiments, said administration is topically to the eye. In further embodiments, said composition is a liquid solution. In further embodiments, said subject is diagnosed with macular degeneration.

In some embodiments, the invention relates to a method of treating or preventing macular degeneration comprising: 1) providing i) a subject that exhibits a symptom of macular degeneration, and in further embodiments said administering causes a reduction in said symptom and ii) a composition comprising a substituted or unsubstituted compound having the formula:

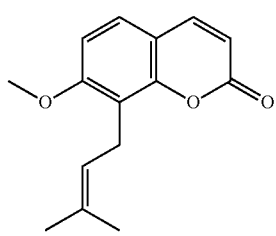

and derivatives thereof and 2) administering said compound to said subject. In further embodiments, said macular degeneration is age-related. In further embodiments, said subject is a human. In further embodiments, said administration is topically to the eye. In further embodiments, said composition is a liquid solution. In further embodiments, said subject is diagnosed with macular degeneration.

In some embodiments, the invention relates to a method of treating or preventing macular degeneration comprising: 1) providing i) a subject diagnosed with or at risk for macular degeneration and ii) a composition comprising a substituted or unsubstituted compound having the formula:

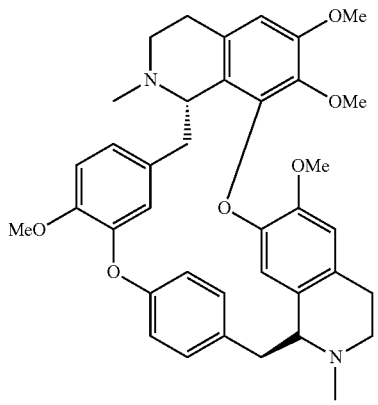

and derivatives thereof functioning to decrease choroidal neovascularization and 2) administering said compound to said subject. In further embodiments, said macular degeneration is age-related. In further embodiments, said subject is a human. In further embodiments, said administration is topically to the eye. In further embodiments, said composition is a liquid solution. In further embodiments, said subject is diagnosed with macular degeneration.

In some embodiments, the invention relates to a method of treating or preventing macular degeneration comprising: 1) providing i) a subject that exhibits a symptom of macular degeneration, and in further embodiments said administering causes a reduction in said symptom and ii) a composition comprising a substituted or unsubstituted compound having the formula:

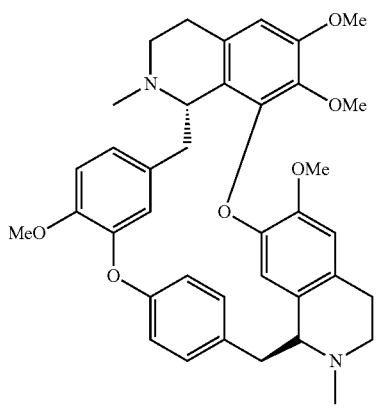

and derivatives thereof functioning to decrease choroidal neovascularization and 2) administering said compound to said subject. In further embodiments, said macular degeneration is age-related. In further embodiments, said subject is a human. In further embodiments, said administration is topically to the eye. In further embodiments, said composition is a liquid solution. In further embodiments, said subject is diagnosed with macular degeneration.

In additional embodiments, the invention relates to a method of managing, prevention, and/or treating age-related macular degeneration comprising: 1) providing i) a subject and ii) a composition comprising a compound functioning to decrease choroidal neovascularization and 2) administering said compound to said subject. In further embodiments, said compound is an interleukin-1 (IL-1) blockers preferably CK-17 (5-bromo-5-methyl-3-phenyl-2-phenylimino-1,3-thiazinan-4-one), CK-112, CK-113, CK-115, CK-116, and CK-117. In further embodiments, said compound is a substituted or unsubstituted compound or derivative of the following structure:

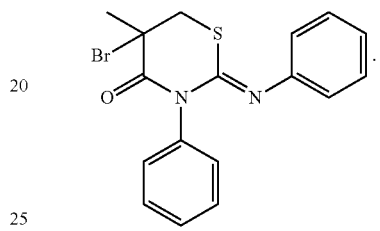

In further embodiments, said compound has the following structure:

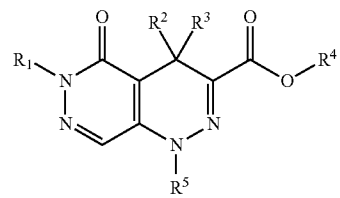

wherein, $R^1$ is hydrogen, alkyl, substituted alkyl, aryl, substituted aryl, arylalkyl, and substituted arylalkyl; $R^2$ and $R^3$ are the same or different and, at each occurrence, independently hydrogen, alkyl, substituted alkyl, alkylcarboxyl or substituted alkylcarboxyl; $R^4$ is hydrogen or alkyl; and $R^5$ is alkyl.

In further embodiments, said compound is selected from the group consisting hydralazine i.e., phthalazin-1-ylhydrazine, quanabenz, i.e., (2-[(2,6-dichlorophenyl)methylideneamino]guanidine, D-timolol, i.e., (2R)-1-[(4-morpholin-4-yl-1,2,5-thiadiazol-3-yl)oxy]-3-(tert-butylamino)propan-2-ol, apigenin i.e., 4,5-dihydroxy-2-(4-hydroxyphenyl)chromen-7-one, naringenin, i.e., 5,7-dihydroxy-2-(4-hydroxyphenyl)chroman-4-one, quercetin, i.e., 2-(3,4-dihydroxyphenyl)-3,4,5-trihydroxy-chromen-7-one, flavon, i.e., 3-hydroxy-2-phenyl-chromen-4-one, DN-6, i.e., N-methoxy-1-nitro-1H-pyrazole-3-carboxamide, DN-7, i.e., 1-nitro-1H-pyrazole-3-carboxylic acid, and DN-13, i.e., 4-bromo-1-nitro-1H-pyrazole or substituted compounds and combinations thereof.

In some embodiments the invention relates to the use of a compound functioning to decrease choroidal neovascularization for the manufacture of a medicament for the treatment of macular degeneration, preferably age-related macular degeneration.

In some embodiments, the invention relates to a compound or derivative of a compound herein functioning as an interleukin-1 blocker used in the treatment or prevention of eye diseases. In further embodiments, said interleutkin-1 blocker is selected from the group consisting of CK-17, CK-112, CK-113, CK-115, CK-116, and CK-117. In further embodiments, said compound is prednisolone. In further embodiments, said compound is a substituted or unsubstituted compound or derivative of the following structure:

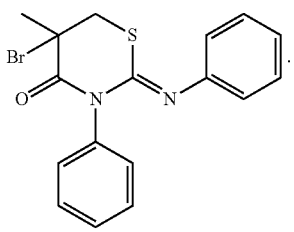

In further embodiments, said compound has the following structure:

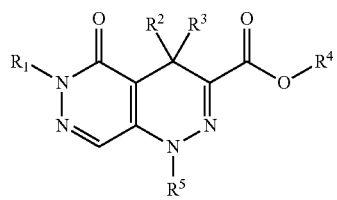

wherein, $R^1$ is hydrogen, alkyl, substituted alkyl, aryl, substituted aryl, arylalkyl, and substituted arylalkyl; $R^2$ and $R^3$ are the same or different and, at each occurrence, independently hydrogen, alkyl, substituted alkyl, alkylcarboxyl or substituted alkylcarboxyl; $R^4$ is hydrogen or alkyl; and $R^5$ is alkyl.

In some embodiments, the invention relates to the use of substituted or unsubstituted compounds disclosed herein or derivatives thereof for the treatment of age-related macular degeneration.

In some embodiments, the present invention provides methods of treating or preventing eye disease comprising administering an IL-1 blocker to a patient with eye-disease such that at least one symptom of the eye disease is reduced or eliminated. In further embodiments, the eye disease is age-related macular degeneration. In some embodiments, the administering is performed via the eye. In certain embodiments, the administering is performed orally or systemically. In further embodiment, the subject is diagnosed or at risk for macular degeneration.

In particular embodiments, the present invention provides compositions comprising; i) an IL-1 blocker, and ii) an ophthalmic solution.

In other embodiments, the present invention provides systems comprising: a) a composition comprising an IL-1 blocker and an ophthalmic solution; and b) an eye-dropper. In particular embodiments, the composition is located in the eye-dropper.

In certain embodiments, the IL-blocker is specific for IL-1 alpha. In other embodiments, the IL-blocker is specific for IL-1 beta. In further embodiments, the IL-1 blocker is selected from the group consisting of CK-17, CK-112, CK-113, CK-115, CK-116, CK-117, CK-101A, CK-103A, CK-119, CK-120, and CK-122, and similar compounds. In other embodiments, the IL-1 blocker is selected from the group consisting of: IL-1 siRNA sequences configured to reduce the expression of IL-1 proteins, a vector configured to express IL-1 siRNA sequences, anti-IL-1 antibodies or fragments, anti-IL1 antisense sequences, and vectors configured to express anti-IL1 antisense sequences.

In some embodiments, the invention relates to a method of treating or preventing age-related macular degeneration comprising: 1) providing i) a subject diagnosed or at risk for macular degeneration and ii) a composition comprising a compound functioning to decrease choroidal neovascularization and 2) administering said compound to said subject. In further embodiments, said compound is an interleukin-1 blocker. In further embodiments, said compound is selected from the group consisting of CK-17, CK-112, CK-113, CK-115, CK-116, CK-117, CK-101A, CK-103A, CK-119, CK-120, and CK-122. In further embodiments, said compound is prednisolone.

In additional embodiments, the invention relates to the use of a compound functioning to decrease choroidal neovascularization for the manufacture of a medicament for the treatment of macular degeneration. Preferably age-related macular degeneration.

In additional embodiments, the invention relates to the use of compound disclosed herein for the manufacture of a medicament for the treatment of age-related macular degeneration. Preferably age-related macular degeneration.

In additional embodiments, the invention relates to the use of a substituted compound disclosed herein functioning to decrease choroidal neovascularization for the manufacture of a medicament for the treatment of age-related macular degeneration. In further embodiments, said compound is an interleukin-1 blocker. In further embodiments, said compound is selected from the group consisting of CK-17, CK-112, CK-113, CK-I 15, CK-116, CK-117, CK-10I A, CK-103A, CK-119, CK-120, and CK-122. In further embodiments, said compound is prednisolone, tetrandrine or osthole or derivative or substituted compound thereof. In further embodiments, said compound is a substituted or unsubstituted compound or derivative of the following structure:

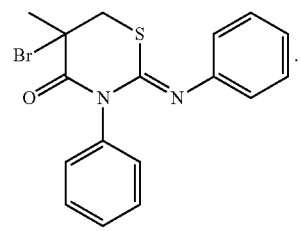

In additional embodiments, the invention relates to the use of a compounds disclosed herein functioning to inhibit IL-1 induced uveitis for the manufacture of a medicament for the treatment of arthritis, preferably rheumatoid arthritis. In further embodiment a subject shows symptoms of arthritis before administration. In further embodiments, said compound is an interleukin-1 blocker. In further embodiments, said compound is selected from the group consisting of CK-17, CK-112, CK-113, CK-115, CK-116, CK-117, CK-101A, CK-103A, CK-119, CK-120, and CK-122. In further embodiments, said compound is prednisolone, tetrandrine or osthole or derivative or substituted compound thereof.

The compositions comprising the active compounds of the present invention may include nutritional/dietary supplements and bulk-drug compositions useful in the manufacture of pharmaceutical compositions (e.g., impure or non-sterile compositions) and pharmaceutical compositions (i.e., compositions that are suitable for administration to a subject) that can be used in the preparation of unit dosage forms. Such compositions optionally comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of the active compound and another therapeutic or prophylactic agent, and a pharmaceutically acceptable carrier. These compositions may contain between 0.1-99% of the active ingredient.

In certain embodiments, the therapeutic compounds (e.g., IL-1 blockers) are in an ophthalmic solution (e.g. such that the blockers can be administered directly to the eye of the patient via an eye dropper). Preferably, the osmotic value of the solution is about 0.9% sodium chloride (e.g. 0.6% to about 1%). It is also preferred that the ophthalmic solution have a pH of about 7.4 (e.g. 6.6 to 7.8, preferably 7.0 to 7.4). It is also preferred that the ophthalmic solution be buffered to prevent wide changes in the pH.

BRIEF DESCRIPTION OF THE DRAWINGS

For a more complete understanding of the features and advantages of the present invention, reference is now made to the detailed description of the invention along with the accompanying figures.

FIG. 12 shows data of blockade of IL-1 Induced Uveitis by Synthetic IL-1 Blockers: *, significantly different from corresponding controls at $p<0.05$ with N=6 eyes and Mean±SEM: **, 10 mg/kg, ip, t.i.d.

FIG. 13 show data of blockade of IL-1 Induced Uveitis by Natural Products: * significantly different from corresponding controls at $p<0.15$ with N=6 eyes and Mean±SEM.

FIG. 14 shows the delay of Trabeculaectomy Failure Caused by Inflammation with Prednisolone and IL-1 Blockers *, significantly larger than control at $p<0.05$ with N=6 eyes and Mean±SEM: ** 10 mg/injection at subTenons FIG. 15 shows data on the affects of aspirin and CK-17 on carrageenin induced inflammation: a, significantly different from controls at $p<0.05$ with n=8 and (Mean±SD): b, significantly different from aspirin at $p<0.05$ with n=8 and (Mean±SD)

FIG. 16 shows data on rabbit irritation responses by 0.1% CK-17 after the eye-drop instillation. Scores are means of 6 eyes: Cornea=degree of opacity; Iris=degree of iritis; Conjunctiva=redness, chemosis, and discharge; Total Cornea, iris, and conjunctiva together; R=right eye (test); L=Left eye (control).

FIG. 18 shows the chemical structures of CK-101A, CK-103A, CK-119, CK-120, and CK-122.

DETAILED DESCRIPTION OF THE INVENTION

Figure 1:
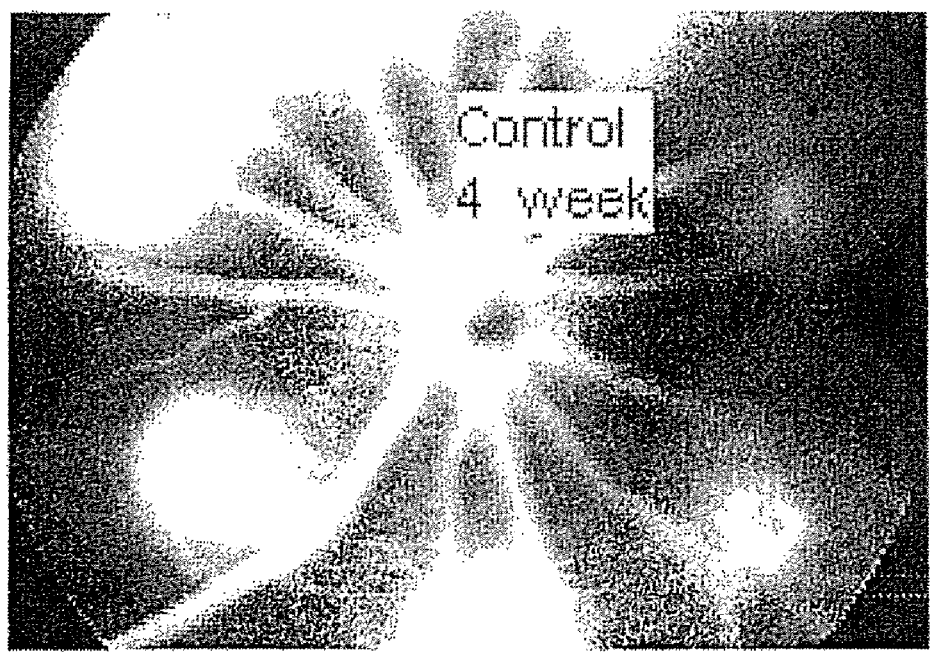
FIG. 1 is a fluorescein angiograph that shows the control formation of choroidal neovascularization (CNV) by using a laser treatment.
Figure 2:
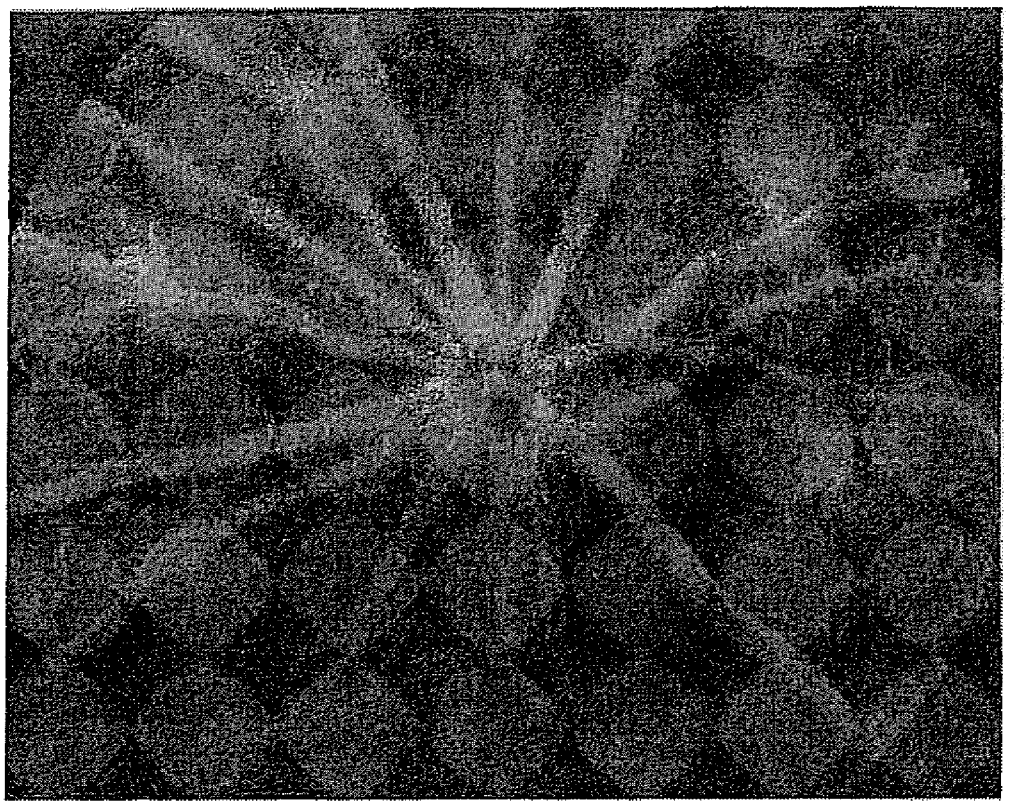
FIG. 2 is a fluorescein angiograph that shows the inhibition of CNV formation by intraperitonal administration of 3 mg/kg 10 mg/kg hydralazine.
Figure 3:
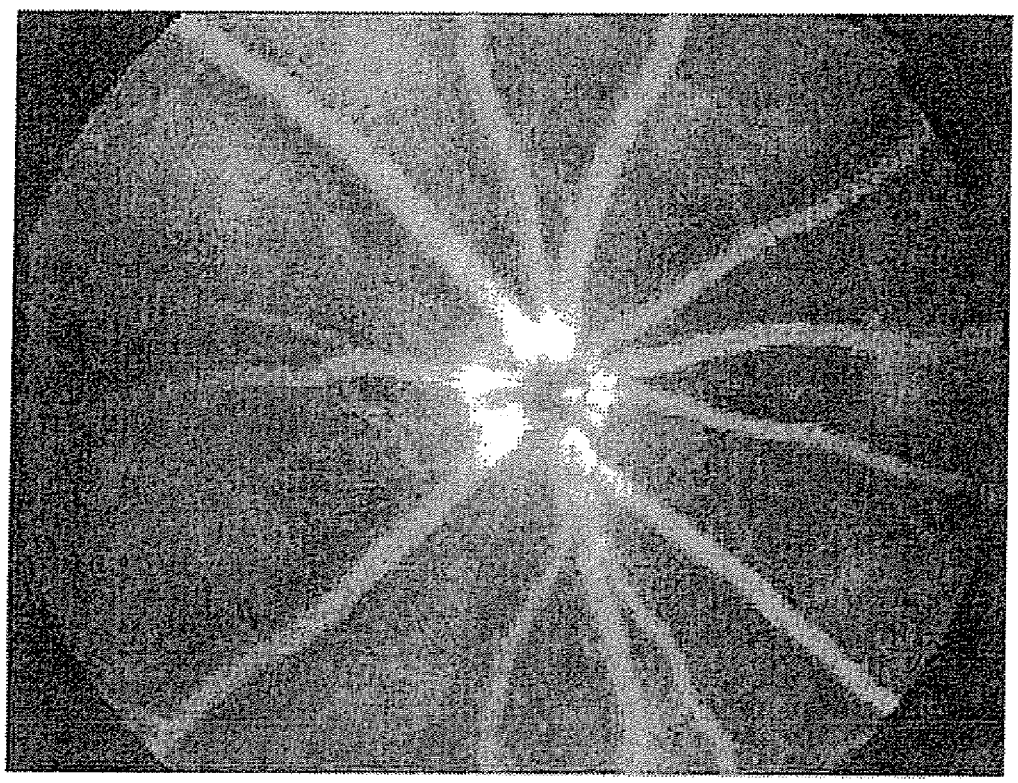
FIG. 3 is a fluorescein angiograph that shows the inhibition of CNV formation by intraperitonal administration of 20 mg/kg guanabenz.

The present invention relates in general to therapeutic compositions and methods of use. In preferred embodiments, the invention relates to the field of eye health. In some embodiments, the invention relates to the prevention and treatment of macular degeneration by administering compounds disclosed herein. In some embodiments, the invention relates to compositions and methods of improving vision.

In some embodiments, the invention relates to the prevention and treatment of age-related macular degeneration by administering compounds disclosed herein. In some embodiments, the invention relates to compositions and methods of improving health including dietary supplements that prevent of choroid ischemic trauma leading to age-related macular degeneration.

Numerous methods have been attempted to treat age-related macular degeneration without success. They include laser photocoagulation for choroidal neovascularization, radiation treatment, transpupillary thermotherapy of subfoveal occult choroidal neovascularization, submacular surgery, limited macular translocation, adjuncts in surgery, argon laser to drusen, infrared diode laser photocoagulation.

Pharmacological treatments have been tried but with very limited success. For example, photodynamic therapy with verteporfin, visudyne, and BPD-MA has been shown to be beneficial for some wet-AMD patients (15%) but not for dry-AMD patients (85%). More recently, newer agents such as vascular endothelial growth factor (VEGF) receptor kinase inhibitors, anti-VEGF antibodies, pigment epithelium-derived factor (PEDF), and angiostatin have been tried to prevent the CNV formation at the very late stage of AMD. They are still in the experimental stage and none have been shown to be efficacious in human patients. Thus, there is a need to identify agents that can be used to manage, prevent, and/or treat age-related macular degeneration.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein an "eye disease" means any variety of diseases, impairments, or defects that cause, vision loss, blurred or decreased central close-up and distance vision, blind spots, objects to appear a different color or shape, neuro-ophthalmic manifestations of vascular eye diseases, including ischemic optic neuropathy, anterior ischemic optic neuropathy, retinal artery occlusion, asymptomatic retinal emboli, asymptomatic retinal embolus or ischemia of retinal tissue, retinal edema, amaurosis fugax, reduction in visual field, occlusion of ocular vessels, stagnation of blood flow within the arteriole, cataracts, glaucoma, proptosis, eyelid retraction, restrictive myopathy, diplopia (double vision), compressive optic neuropathy, and/or exposure keratopathy. In a preferred embodiment, the eye disease is macular degeneration or diabetic eye disease. It is not intended that the present invention be limited to treating any particular underlying disease resulting in vision defects or impairments.

As used herein, "macular degeneration" means any condition that causes part of the macula to deteriorate. This degeneration may be partial or total, and it is not intended to be limited to advance stages of the disease: thus, is intended to include a subject that is diagnosed with drusen even thought the subject does not have any symptoms of impaired vision. A symptom of macular degeneration is a change in central vision. The patient may notice blurred central vision or a blank spot on the page when reading. The patient may notice visual distortion such as bending of straight lines. Images may appear smaller. Some patients notice a change in color perception and some experience abnormal light sensations. These symptoms may come on suddenly and become progressively more troublesome. Sudden onset of symptoms, particularly vision distortion, is an indication for immediate evaluation by an ophthalmologist.

As used herein a diagnosis of macular degeneration means any analysis of macular changes or function in a subject. It is not intended to be limited to any particular method. For example, an eye examiner, e.g., doctor, may dilate the pupil with eye drops and examine the interior of the eye, looking at the retina for the presence of yellow bumps of drusen, eye lesions, or for gross changes in the macula such as thinning. The eye examiner may also administer a visual field test, looking for blank spots in the central vision. The examiner may call for fluorescein angiography (intravenous injection of fluorescent dye followed by visual examination and photography of the back of the eye) to determine if blood vessels in the retina are leaking.

Some risk factors for having macular degeneration include, age, smoking, and a diet that is rich in saturated fat. Others may be at risk for macular degeneration because of genetic heritage or environmental exposure. In preferred embodiments, the invention relates to treating or prevention of age-related macular degeneration, preferably prophylactic prevention and treatment.

Age-related macular degeneration may be characterized as a dry (atrophic) or wet (exudative) form. Multiple, small, round, yellow-white spots called drusen are identifiers for the dry type. The spots are typically located in the back of the eye at the level of the outer retina. Subjects with these spots may have excellent vision and no symptoms. Most subjects with age-related macular degeneration begin with the dry form. In the wet form, newly created abnormal blood vessels grow under the center of the retina. These blood vessels leak, bleed, and scar the retina, distorting vision or destroying central vision. Vision distortion may starts in one eye and may affect the other eye later.

A diabetic (Type I or Type II) patient is at risk for macular degeneration. Diabetic macular degeneration is the deterioration of the macula due to diabetes. Cystoid macular degeneration is the loss of vision in the macula due to fluid-filled areas (cysts) in the macular region. This may be a result of other disorders, inflammation, or high myopia.

As used herein, a compound "functioning to decrease choroidal neovascularization" means that a statistically significant reduction of choroidal neovascularization can be measured, e.g. by fluorescein angiography, after some period of time of administering said compound to a mammalian after physical disruption of the eye's Bruch's membrane, e.g., via a laser. A detailed description of these methods for identifying compounds functioning to decrease choroidal neovascularization are describe herein.

"Isomers" means any of two or more substances that are composed of the same elements in the same proportions but differ in the three dimensional arrangement of atoms including enantiomeric (i.e., mirror images) and diastereomeric isomers.

"Timolol compound" or molecules, and the like means substituted or unsubstituted compounds of the following formula:

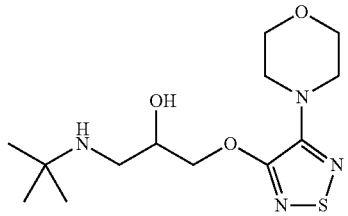

As used herein, the term "timolol component" refers that part of a composition that contains all of timolol molecules in a given composition, including all conformational and stereomeric forms. In preferred embodiments, a given compound (e.g. designated by a structure) makes up a large percentage (e.g. by number of molecules and/or by weight) of the timolol component. For example, a given timolol derivative may be present in an aqueous composition at a level where 70% of all the timolol components are of that given compound, e.g. D-Timolol, while most of the composition itself is composed of water.

The term "salts", as used herein, refers to any salt that complexes with identified compounds contained herein while retaining a desired function, e.g., biological activity. Examples of such salts include, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Salt compounds can also be administered as pharmaceutically acceptable quaternary salts known by a person skilled in the art, which specifically include the quaternary ammonium salts of the formula —NR,R',R"+Z−, wherein R, R', R" is independently hydrogen, alkyl, or benzyl, and Z is a counter ion, including, but not limited to, chloride, bromide, iodide, alkoxide, toluencsulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Adverse drug reaction" means any response to a drug that is noxious and unintended and occurs in doses for prophylaxis, diagnosis, or therapy including side effects, toxicity, hypersensitivity, drug interactions, complications, or other idiosyncrasy. Side effects are often adverse symptom produced by a therapeutic serum level of drug produced by its pharmacological effect on unintended organ systems (e.g., blurred vision from anticholinergic antihistamine). A toxic side effect is an adverse symptom or other effect produced by an excessive or prolonged chemical exposure to a drug (e.g., digitalis toxicity, liver toxicity). Hypersensitivities are immune-mediated adverse reactions (e.g., anaphylaxis, allergy). Drug interactions are adverse effects arising from interactions with other drugs, foods or disease states (e.g., warfarin and erythromycin, cisapride and grapefruit, loperamide and *Clostridium difficile* colitis). Complications are diseases caused by a drug (e.g., NSAID-induced gastric ulcer, estrogen-induced thrombosis). The adverse drug reaction may be mediated by known or unknown mechanisms (e.g., Agranulocytosis associated with chloramphenicol or clozapine). Such adverse drug reaction can be determined by subject observation, assay or animal model well-known in the art.

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkylamino" and "dialkylamino" mean one or two alkyl moiety attached through a nitrogen bridge (i.e., —N-alkyl) such as methylamino, ethylamino, dimethylamino, diethylamino, and the like.

"Alkylcarboxyl" means an alkyl moiety attached through a carboxyl group (i.e., $CO_2$Alkyl).

"Alkylcarboxyl" means an alkyl moiety attached through a carbonyl group (i.e., —(C=O)Alkyl). A "succinyl" is an ethylcarbonyl substituted with a carboxyl group on the second carbon (i.e., —(C=O)$CH_2CH_2CO_2H$).

"Alkylthiol" means an alkyl moiety attached through a sulfur bridge (i.e., —S-alkyl).

"Alkyloxy" means an alkyl moiety attached through an oxygen bridge (i.e., —O-alkyl) such as methoxy, ethoxy, and the like.

"Alkoxide" means an alkyl moiety attached to a negatively charged oxygen atom (i.e., —Oalkyl) such as methoxide or ethoxide.

Within the context of certain embodiment, an "amine" group means —$NH_2$, and "ammonia" means the gas $NH_3$.

"Aryl" means an aromatic carbocyclic moiety such as phenyl or naphthyl.

"Arylalkyl" means an aryl moiety attached through an alkyl bridge (e.g., —$CH_2$-Phenyl).

"Aryloxy" means an aryl moiety attached through an oxygen bridge (i.e., —O-aryl).

"Arylthio" means an alkyl moiety attached through a sulfur bridge (i.e., —S-aryl).

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —$CH_2$morpholinyl, and the like.

"Homocycle" (also referred to herein as "homocyclic ring") means a saturated or unsaturated (but not aromatic) carbocyclic ring containing from 3-7 carbon atoms, such as cyclopropane, cyclobutane, cyclopentane, cyclohexane, cycloheptane, cyclohexene, and the like.

"Isomers" means any of two or more substances that are composed of the same elements in the same proportions but differ in the three dimensional arrangement of atoms including enantiomeric (i.e., mirror images) and diastereomeric isomers.

The term "derivative" when used in relation to a chemical compound refers to a similar structure that upon application, e.g., administration to a subject, is capable of providing, directly or indirectly, the function said chemical compound is disclosed to have (albeit the derivative may have increased or decreased function). For example, substituting one atom for another atom in a chemical compound provides a compound of similar structure, e.g., a carbon atom for a nitrogen atom. The compound of similar structure may be capable of functioning to decrease choroidal neovascularization. Certain claimed embodiments are intended to encompass minor changes in chemical structure provided that the derivative can decrease choroidal neovascularization.

The term "manage" when used in connection with a disease or condition means to provide beneficial effects to a subject being administered with a prophylactic or therapeutic agent, which does not result in a cure of the disease. In certain embodiments, a subject is administered with one or more prophylactic or therapeutic agents to manage a disease so as to prevent the progression or worsening of the disease.

As used herein, the terms "prevent" and "preventing" include the prevention of the recurrence, spread or onset. It is not intended that the present invention be limited to complete prevention. In some embodiments, the onset is delayed, or the severity of the disease is reduced.

"Subject" means any animal, preferably a human patient, livestock, or domestic pet.

The term "substituted", as used herein, means at least one hydrogen atom of a molecular arrangement is replaced with a substituent. In the case of an oxo substituent ("=O"), two hydrogen atoms are replaced. When substituted, one or more of the groups below are "substituents." Substituents within the context of this invention include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle, and heterocyclealkyl, as well as, —$NR_aR_b$, —$NR_aC(=O)R_b$, —$NR_aC(=O)NR_aNR_b$, —$NR_aC(=O)OR_b$—$NR_aSO_2R_b$, —$C(=O)R_a$, $C(=O)OR_a$, —$C(=O)NR_aR_b$, —$OC(=O)NR_aR_b$, —$OR_a$, —$SR_a$, —$SOR_a$—$S(=O)_2R_a$, —$OS(=O)_2R_a$, and —$S(=O)_2OR_a$. In addition, the above substituents may be further substituted with one or more of the above substituents, such that the substituent comprises a substituted alky, substituted aryl, substituted arylalkyl, substituted heterocycle, or substituted heterocyclealkyl. $R_a$ and $R_b$ in this context may be the same or different and, independently, hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

The term "unsubstituted", as used herein, refers to any compound does not contain extra substituents attached to the compound. An unsubstituted compound refers to the chemical makeup of the compound without extra substituents, e.g., the compound does not contain protecting group(s). For example, unsubstituted proline is a proline amino acid even though the amino group of proline may be considered disubstituted with alkyl groups.

With regard to certain embodiments, a chemical structure may be drawn with two lines between a first atom and substituent meaning that there are two bonds, i.e., designate a double between the first atom and a defined substituent or it may designate two single bonds between the first atom and two defined substituent atoms.

As used herein, the terms "treat" and "treating" are not limited to the case where the subject (e.g. patient) is cured and the disease is eradicated. Rather, the present invention also contemplates treatment that merely reduces symptoms, improves vision (to some degree) and/or delays disease progression.

As used herein, the term "IL-1 blocker" refers to any compound or composition that is able to at least partially inhibit the biological activity or expression of IL-1a and/or IL-1b in the eye of a patient. In certain embodiments, IL-1 blockers bind to IL-1 proteins or RNA transcripts. In other embodiments, IL-1 blockers competitively inhibit the activity of IL-1 proteins. In further embodiments, the IL-1 blockers destroy IL-1 proteins through cleavage. In some embodiments, the IL-1 blockers cleave or bind to IL-1 mRNA transcripts. Examples of IL-1 blockers include, but are not limited to, CK-17 (5-bromo-5-methyl-3-phenyl-2-phenylimino-1,3-thiazinan-4-one), CK-112, CK-113, CK-115, CK-116, CK-117, IL-1 siRNA sequences and vectors expressing IL-1 siRNA sequences, IL-1 antisense sequences and vectors expressing IL-1 antisense sequences, anti-IL-1 antibodies and fragments thereof, including chimeric and preferably humanized or human anti-IL-1 antibodies. Nucleic acid based IL-1 blockers, such as siRNA and antisense can be designed, for example, using the human IL-1a sequence (accession no. BC013142) or the human IL-1b sequence (accession number BC008678) using techniques and software that are known in the art. Antibody based IL-1 blockers, such as anti-IL-1a or anti-IL-1b monoclonal antibodies can be generated using the human IL-1a protein sequence (accession no. CAG33695) or the human IL-1b protein sequence (accession no. CAG28607) using techniques known in the art.

The term "siRNAs" refers to short interfering RNAs. In some embodiments, siRNAs comprise a duplex, or double-stranded region, of about 18-25 nucleotides long. Often siRNAs contain from about two to four unpaired nucleotides at the 3' end of each strand. At least one strand of the duplex or double-stranded region of a siRNA is substantially homologous to or substantially complementary to a target RNA molecule, such as IL-1 mRNA transcripts. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene (e.g. IL-1a or IL-1b) may be endogenous or exogenous to the organism, present integrated into a chromosome or present in a transfection vector that is not integrated into the genome. The expression of the gene (e.g. IL-1a) is either completely or partially inhibited. RNAi may also be considered to inhibit the function of a target IL-1 RNA; the function of the target IL-1 RNA may be complete or partial.

Aging is a chronic process to cause degeneration of cells, tissues, and organs, including choroidal blood vessels, retinal pigment epithelium cells (RPEC) and Bruch's membrane of macular. Most notably arteriosclerotic aging changes choroidal blood vessels, particularly the macular chorio-capillaris with a decrease in total capillary membrane and the blood flow. As a result, RPE starts to accumulate lipofuscin, alters cell shape, density, pigmentation, lysosomal activity and extracellular matrix formation. Gradually, Bruch's membrane shows thickening and decreased permeability, resulting with breakdown of Bruch's membrane which allows choroidal neovascularization (CNV) to appear.

Since CNV is formed because of vascular inflammation, others have tried to use VEGF receptor kinase inhibitors, anti-VEGF antibodies, PEDF and angiostatin to prevent the CNV formation and AMD worsening. The problem is these agents are used to remove only one of many inflammatory factors and thus the efficacy is not obvious unless all these agents are administered at the same time. While not necessary to understand or practice the present invention, it is believed that a factor of vascular inflammation is caused by IL-1 and thus if IL-1 blockers are given, the vascular inflammation is decreased The breakdown of Bruch's membrane enables the growth of CNV into subfoveal space. Agents which stabilize Bruch's membrane also prevent it from breakdown and the penetration of CNV into the subfoveal space. As it is believed that IL-1 causes pathological changes of Bruch's membrane, IL-1 blockers stabilize it and prevent it from breaking down. Therefore, in certain embodiments, I1-1 blockers serve as double edge sword to prevent vascular inflammation and Bruch's membrane breaking down so that CNV formation and spreading can be prevented and, in turn, so does AMD.

It is recognized that AMD preferably is treated at the earliest stage possible to prevent disease progression. The earliest stage of AMD development is the malfunction of choroidal blood flow, resulting in a decrease of the blood flow of choriocapillaris. Chain reactions are triggered that lead to RPE degenerations, Bruch's membrane breakdown, CNV formation, AMD and finally blindness. Therefore, specific drugs that increase the choroidal blood flow were found herein to be useful to prevent the AMD from developing and worsening. The agents discovered include, but are not limited to: hypotensive agents (e.g., timolol, hydralazine guanaben); flavonoids (e.g., Apigenin, Naringenin Quercetin, Flavon); and N-nitro-pyrazoles and C-nitro-pyrazoles (e.g., DN-6, CN-7, DN-13, and DC-5).

Pharmaceutical Formulations

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155).

In a preferred embodiment, the active compound and optionally another therapeutic or prophylactic agent are formulated in accordance with routine procedures as pharmaceutical compositions adapted for intravenous administration to human beings. Typically, the active compound for intravenous administration are solutions in sterile isotonic aqueous buffer. Where necessary, the compositions can also include a solubilizing agent. Compositions for intravenous administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the active compound is to be administered by infusion, it can be dispensed, for example, with an infusion bottle containing sterile pharmaceutical grade water or saline. Where the active compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for an orally administered of the active compound. in these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade.

Further, the effect of the active compound can be delayed or prolonged by proper formulation. For example, a slowly soluble pellet of the active compound can be prepared and incorporated in a tablet or capsule. The technique can be improved by making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound in oily or emulsified vehicles which allow it to disperse only slowly in the serum.

Compositions for use in accordance with the present invention can be formulated in conventional manner using one or more physiologically acceptable carriers or excipients.

Thus, the compound and optionally another therapeutic or prophylactic agent and their physiologically acceptable salts and solvates can be formulated into pharmaceutical compositions for administration by inhalation or insufflation (either through the mouth or the nose) or oral, parenteral or mucosol (such as buccal, vaginal, rectal, sublingual) administration. In some embodiments, the administration is optical (e.g. eyes drops applied directly to the eye). In one embodiment, local or systemic parenteral administration is used.

For oral administration, the compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional mariner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compositions can be formulated for parenteral administration by injection, e.g., by bolus injection or continuous infusion. Formulations for injection can be presented in unit dosage form, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the active ingredient can be in powder Rhin for constitution with a suitable vehicle, e.g., sterile pyrogen-free water, before use.

In addition to the formulations described previously, the compositions can also be formulated as a depot preparation. Such long acting formulations can be administered by implantation (for example subcutaneously or intramuscularly) or by intramuscular injection. Thus, for example, the pharmaceutical compositions can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

In certain preferred embodiments, the pack or dispenser contains one or more unit dosage forms containing no more than the recommended dosage formulation as determined in the Physician's Desk Reference ($56^{th}$ ed. 2002, herein incorporated by reference in its entirety).

Methods of administering the active compound and optionally another therapeutic or prophylactic agent include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, the active compound and optionally another prophylactic or therapeutic agents are administered intramuscularly, intravenously, or subcutaneously. The active compound and optionally another prophylactic or therapeutic agent can also be administered by infusion or bolus injection and can be administered together with other biologically active agents. Administration can be local or systemic. The active compound and optionally the prophylactic or therapeutic agent and their physiologically acceptable salts and solvates can also be administered by inhalation or insufflation (either through the mouth or the nose). In a preferred embodiment, local or systemic parenteral administration is used.

In specific embodiments, it can be desirable to administer the active compound locally to the area in need of treatment. This can be achieved, for example, and not by way of limitation, by local infusion during surgery or topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the active compound can be formulated as a suppository, with traditional binders and vehicles such as triglycerides.

In another embodiment, the active compound can be delivered in a vesicle, in particular a liposome.

In yet another embodiment, the active compound can be delivered in a controlled release system. In one embodiment, a pump can be used. In another embodiment, polymeric materials can be used.

The amount of the active compound that is effective in the treatment or prevention of age-related macular degeneration can be determined by standard research techniques. For example, the dosage of the active compound which will be effective in the treatment or prevention of age-related macular degeneration can be determined by administering the active compound to an animal in a model such as, e.g., the animal models known to those skilled in the art. In addition, in vitro assays can optionally be employed to help identify optimal dosage ranges.

Selection of a particular effective dose can be determined (e.g., via clinical trials) by a skilled artisan based upon the consideration of several factors which will be known to one skilled in the art. Such factors include the disease to be treated or prevented, the symptoms involved, the subject's body mass, the subject's immune status and other factors known by the skilled artisan.

The dose of the active compound to be administered to a subject, such as a human, is rather widely variable and can be subject to independent judgment. It is often practical to administer the daily dose of the active compound at various hours of the day. However, in any given case, the amount of the active compound administered will depend on such factors as the solubility of the active component, the formulation used, subject condition (such as weight), and/or the route of administration.

The general range of effective amounts of the active compound alone or in combination with another prophylactic or therapeutic agent(s) are from about 0.001 mg/day to about 1000 mg/day, more preferably from about 0.001 mg/day to 750 mg/day, more preferably from about 0.001 mg/day to 500 mg/day, more preferably from about 0.001 mg/day to 250 mg/day, more preferably from about 0.001 mg/day to 100 mg/day, more preferably from about 0.001 mg/day to 75 mg/day, more preferably from about 0.001 mg/day to 50 mg/day, more preferably from about 0.001 mg/day to 25 mg/day, more preferably from about 0.001 mg/day to 10 mg/day, more preferably from about 0.001 mg/day to 1 mg/day. Of course, it is often practical to administer the daily dose of compound in portions, at various hours of the day. However, in any given case, the amount of compound administered will depend on such factors as the solubility of the active component, the formulation used, subject condition (such as weight), and/or the route of administration.

Choroidal Blood Flow

Naringenin is a flavon analog with potent effects to increase the choroidal blood flow as can be seen in Table 1. The blood flow increased rapidly at 30 min after drug administration. The effect peaked at 60 min after drug administration and maintained the drug action for at least 2 hrs. At the peak, the choroidal blood flow was increased more than 200% of the original blood flow.

Apigenin is a flavon analog. The drug actions lasted from 1 hr to 2 hrs after administration (Table 1).

Puerarin is also a flavon analog similar to apigenin. Puerarin's action started from 1 hr after administration and lasted beyond 3 hrs after administration (Table 1).

TABLE 1

Effects of Flavonoids on Choroidal Blood Flow

| Compounds (50 μl, 1%) | 30 min | 60 min | 120 min | 180 min |
| --- | --- | --- | --- | --- |
| Vehicle | 100[a] | 100[b] | 100[c] | 100[d] |
| Naringenin | 102.5 ± 22.0[e]* | 226.1 ± 55.0* | 124.2 ± 74.5* | 137.4 ± 712 |
| Apingenin | 9.7 ± 1.5 | 180.1 ± 42.2* | 54.8 ± 6.7* | −II 1 ± 2.3 |
| Puerarin | 30.9 ± 7.7 | 114.9 ± 21.5* | 160.8 ± 70.7* | 127.4 ± 65.5* |

*Significantly higher than corresponding controls at 100%
[a]5.9 ± 0.7 μl/min/mg;
[b]3.89 + 0.7 μl/min/mg;
[c]2.2 ± 0.5 μl/min/mg;
[d]1.71 + 0.5 μl/min/mg;
[e]mean ± SD with N = 6 for all except N = 10 for controls.

N-Nitropyrazoles, including DN-6, DN-7, DN-12, and DN-13 showed very strong increase of choroidal blood flow and long duration of action lasting beyond 3 hrs after drug administration (Table 2). DN-13 was particularly good as it acted rapidly to increase choroidal blood flow at 30 min after drug administration and the action lasted more than 3 hrs after drug administration (Table 2). Among C-nitropyrazoles, DC-5 showed the most promising actions with short latent period of less than 30 min and long duration of action lasting longer than 3 hrs (Table 2).

TABLE 2

Effects N-nitro-azoles and C-nytropyrazoles on Choroidal Blood Flow

| Compounds (50 μl, 1%) | 30 min | 60 min | 120 min | 180 min |
| --- | --- | --- | --- | --- |
| Vehicle | 100[a] | 100[b] | 100[c] | 100[d] |
| DN-6 | 56.9 ± 17.5[e] | 61.8 + 20.9* | 88.3 ± 34.1* | 128.5 ± 60.0* |
| DN-7 | 42.0 + 13.7 | 57.2 ± 3.7* | 80.5 ± 23.1* | 87.3 ± 29.6* |
| DN-12 | 62.9 ± 29.6 | 88.1 + 37.5* | 88.9 ± 32.9* | 32.2 + 15.0 |
| DN-13 | 105.8 ± 30.1* | 83.8 ± 11.3* | 153.3 ± 51.5* | 112.5 ± 34.6* |
| DC-5 | 71.4 ± 33.3* | 71.4 ± 33.3* | 80.3 ± 23.7* | 124.4 ± 25.4* |

*Significantly higher than corresponding controls at 100%
[a]6.9 ± 3.8 μl/min/mg;
[b]7.0 ± 2.9 μl/min/mg;
[c]5.6 ± 1.7 μl/min/mg;
[d]4.9 ± 1.9 μl/min/mg;
[e]mean ± SD with N = 6 for all except N = 10 for controls.

Since these compounds are able to increase choroidal blood flow effectively, it is expected that they can suppress the triggering effect of choroidal ischemia to induce AMD.

Retinal Function Recovery After Ischemic Insult. When the blood flow to the retina was cut off for 30 min, the b-wave of the electoretinogram disappeared, indicating the retinal function was lost. After reperfusion of the retinal blood vessels, however, the b-wave recovered partially to approximately 30-35% of the original level (Tables 3 and 4). The retinal function recovery can be enhanced/facilitated by flavonoids, including naringenin, apigenin and puerarin (Table 3). Among them puerarin showed the best result by showing 90% of retinal function recovery as compared to control recovery of only 31% (Table 3).

TABLE 3

Effects of Flavonoids on Retinal Function Recovery After Ischemic Insult

| Compounds (10 mg/kg ip) | Control | Treated | Net increase (%) |
| --- | --- | --- | --- |
| Naringenin | 32.5 ± 7.5 | 54.0 ± 17.8* | 66.1 |
| Apingenin | 32.5 ± 7.5 | 63.8 ± 12.5* | 96.3 |
| Puerarin | 31.0 ± 9.5 | 90.0 ± 17.2* | 190.3 |

*Significantly higher than corresponding controls at P < 0.05 with N = 6 and Mean + SD N-Nitropyrazoles and C-nytropyrazoles also showed strong retinal function recovery after ischemic insult (Table 4). In general N-nitropyrazoles were more potent than C-nitropyrazoles to facilitate/enhance retinal function recovery after ischemic insult, except DC-5 which showed stronger effects than any other N-nitropyrazoles to facilitate the retinal function recovery after ischemic insult (Table 4).

TABLE 4

Effects of N-Nitropyrazoles and C-Nitropyrazoles on Retinal Function Recovery After Ischemic Insult

| Compounds (10 mg/kg ip) | Control | Treated | Net increase (%) |
|---|---|---|---|
| DN-6 | 32.9 ± 14.2 | 64.0 ± 24.9* | 94.5 |
| DN-7 | 32.9 ± 14.2 | 71.4 ± 20.2* | 117.0 |
| DN-12 | 32.9 ± 14.2 | 58.2 ± 16.7* | 76.9 |
| DN-13 | 35.0 ± 13.1 | 58.6 ± 21.4* | 67.4 |
| DC-5 | 33.0 ± 8.6 | 73.0 ± 16.0* | 120.6 |

*Significantly higher than corresponding controls at $P < 0.05$ with $N = 6$ and Mean ± SD These results indicate that they are potent agents to enhance retinal function recovery possibly though the increase of retinal and choroidal blood flow and are beneficial for the treatment of AMD.

Prevention of CNV Formation

Four weeks after laser treatment of rat's retina to break Bruch's membrane, choroidal neovascularization was formed and was visible with fluorescein angiography as controls.

A number of agents which can improve choroidal blood flow were administered intraperitoneally once a day for 4 weeks. The first type of agents tested were hypotensive agents including hydralazine, guanabenz, and D-Timolol. Hydralazine at 10 mg/kg inhibited all CNV formation effectively. When the dose of hydralazine was reduced to 5 mg/kg, only four out of eight CNV formation were clearly inhibited as compared to the control. Guanabenz was equally effective at 20 mg/kg i.p. All eight CNV formations were inhibited by guanabenz as compared to the control. D-Timolol at 15 mg/kg i.p. was effective in inhibiting some CNV formation but not as potent as hydralazine or guanabenz.

Another group of agents tested was flavonoids, including but not limited to apigenin, naringenin, quercetin, and flavon. Apigenin at 30 mg/kg i.p. showed a potent inhibition on at least six out of eight CNV formations. Naringenin (30 mg/kg i.p.), quercetin (30 mg/kg i.p.), and flavon (20 mg/kg i.p.) showed marked inhibition of CNV formation. Flavon was particularly potent and almost completely inhibited the CNV formation.

Another group of agents tested included N-nitropyrazoles (DN's) which release NO to cause vasodilation and choroid blood flow facilitation. All agents, including DN6, DN7 and DN13 at 20 mg/kg i.p. caused marked inhibition of the CNV formation.

Ischemia of choroidal blood flow is closely related to the induction/triggering of AMD. Therefore, agents that are able to increase choroidal blood flow will be able to prevent choroidal ischemia and the triggering of AMD.

It is known that choroidal ischemia can cause RPE cell degeneration, lipofusion accumulation, lyposomal activity changes and extracellular matrix formation. Further, Bruch's membrane shows abnormality, thickening, and decreases in permeability that leads to the breakdown of the Bruch's membrane and the growth of CNV into the subfoveal areas. As a result visual activity suffered and the AMD developed which leads to the blindness. Therefore, agents that can increase choroidal blood flow (Tables 1 and 2) should be able to prevent/treat AMD from continuing to develop, if they are administered at the early stage of AMD.

The effectiveness of these agents to prevent/treat AMD was further supported by the fact that they can facilitate/enhance retinal and choroidal function recovery after ischemic insult (Tables 3 and 4). Therefore, these agents can be used to treat/prevent AMD formation at the early stage of the disease.

The direct evidence of these agents to prevent/treat AMD comes from the AMD rat model that develop CNV by breakdown of Bruck's membrane by laser beam. Treatment of these AMD animal model with 1) hypotensive agents such as hydralazine, guanabenz, and D-timolol; 2) flavonoids including apigenin, naringenin, quercetin, and flavon; and 3) N-nitropyrazole derivatives such as DN-6, DN-7, DN-13 at various dose levels showed potent inhibition of CNV formation which is the main etiology of AMD formation.

In preferred embodiments, agents as IL-1 blockers are antagonists of IL-1 induced uveitis. Intravitreal injection of IL-1 induced ocular inflammation causes breakdown of the blood-aqueous barrier. As a result, fluorescein may cross the broken blood-aqueous barrier to enter the eye and to reach peak inflammation 12 hr after IL-1 injection. IL-1 is the most potent cytokine to induce inflammation which can be blocked effectively by prednisolone at 20 mg/kg t.i.d. (FIG. 13). Among CK-compounds studied, 9 compounds showed potent blocking effects on IL-1 induced uveitis. Although the dose (10 mg/kg t.i.d.) of these compounds was only half of that of prednisolone (20 mg/kg t.i.d.) used, they produced a similar level of IL-1 blockade as compared to prednisolone (FIGS. 12 and 13). CK-120 was particularly potent to block IL-1 induced uveitis as can be seen from FIG. 12.

Some natural products isolated from Chinese herbs were also quite potent to inhibit IL-1 induced uveitis (FIG. 13). Although tetrandrine is slightly less potent than osthol, it is more important because it produces much less side effects and can be safer when it is used clinically. Therefore, these agents can be used to stabilize Bruch's membrane and to prevent CNV and AMD development.

In preferred embodiments, IL-2 blockers delay trabeculectomy failure caused by Inflammation. Trabeculectomy is used frequently for the treatment of narrow/closed angle glaucoma. However, it causes inflammation and failure of aqueous humor drainage after a short period of time after surgery. The synthetic IL-1 blockers such as CK-17, CK-101A and CK-103A prolonged the appearance of trabeculectomy failure through inhibition of inflammation caused by IL-1 released from surgery (FIG. 14). They were all more effective than prednisolone to delay the trabeculectomy failure (FIG. 14). Thus, these agents could be used to prevent breakdown of Bruch's membrane and the development of CNV and AMD.

In preferred embodiments, IL-1 blockers inhibition of systemic inflammation induced by carrageenin. Carrageenin is a potent inflammatory agent to cause pain and swelling on the joints. IL-1 blockers such as CK-17 was very effective in inhibiting carrageenin induced inflammation (FIG. 15). CK-17 was about 10 times as potent as aspirin which is a standard agent used widely as anti-inflammatory, analgesic, and anti-arthritis drug (Table 15). These results indicate that IL-1 blockers can be used locally as well as systematically for the prevention of inflammation and thus beneficial for the inhibition of CNV formation and AMD development.

In preferred embodiments, IL-1 blockers are therapeutically safe. The $LD_{50}$ of both CK-17 was extremely high, at least 20 g/kg orally, which is equivalent to 1,400 g/70 kg for man. Since the $ED_{50}$ of these compounds was approximately 10 mg/kg, the therapeutic index ($LD_{50}/ED_{50}$) would be higher than 2,000 (20,000 mg/kg±10 mg/kg). One of the safest agents available.

In preferred embodiment, 1L-1 blockers provide negligible eye irritation. The ocular irritation of CK compounds was very low and negligible as can be seen from the Draize test (FIG. 15). This is particularly important because the agents are to be used for the treatment of eye disease, AMD.

In preferred embodiment, IL-1 Mocker suppress of CNV formation in rat eyes. When the Bruch's membrane was broken by laser beam, massive CNV was formed with marked fluorescein leakage in the fluorescein angiography as a control. When the animals were treated by prednisolone at 3 mg/kg i.p. the CNV formation was markedly inhibited five out of eight CNV formations.

Figure 4:
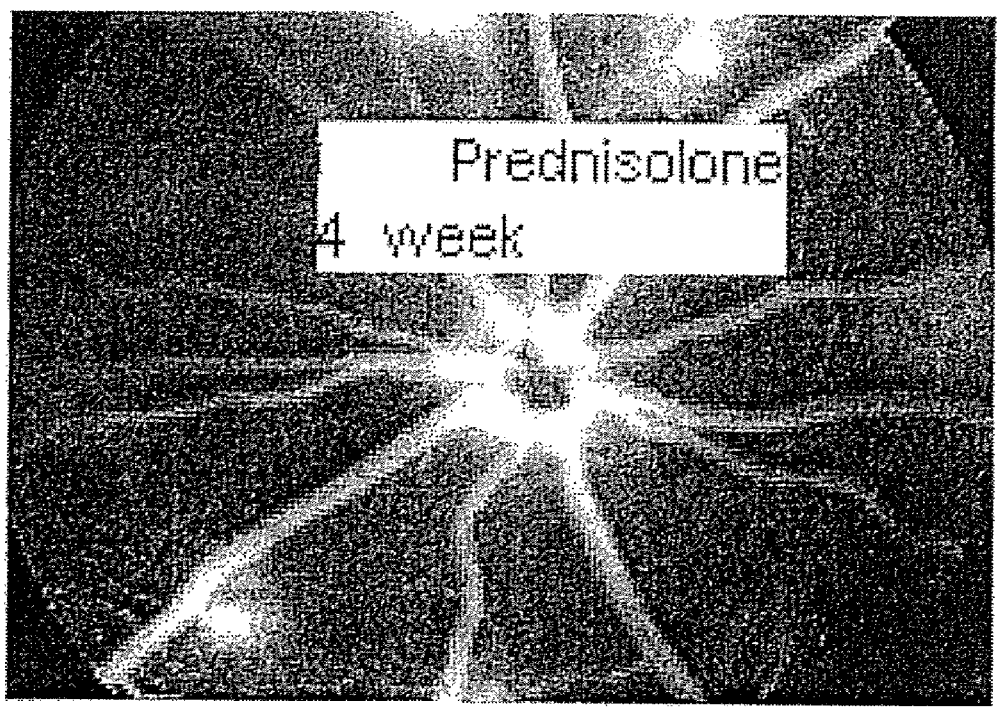
FIG. 4 is a fluorescein angiograph that shows the inhibition of CNV formation by intraperitonal administration of 3 mg/kg prednisolone.
Figure 5:
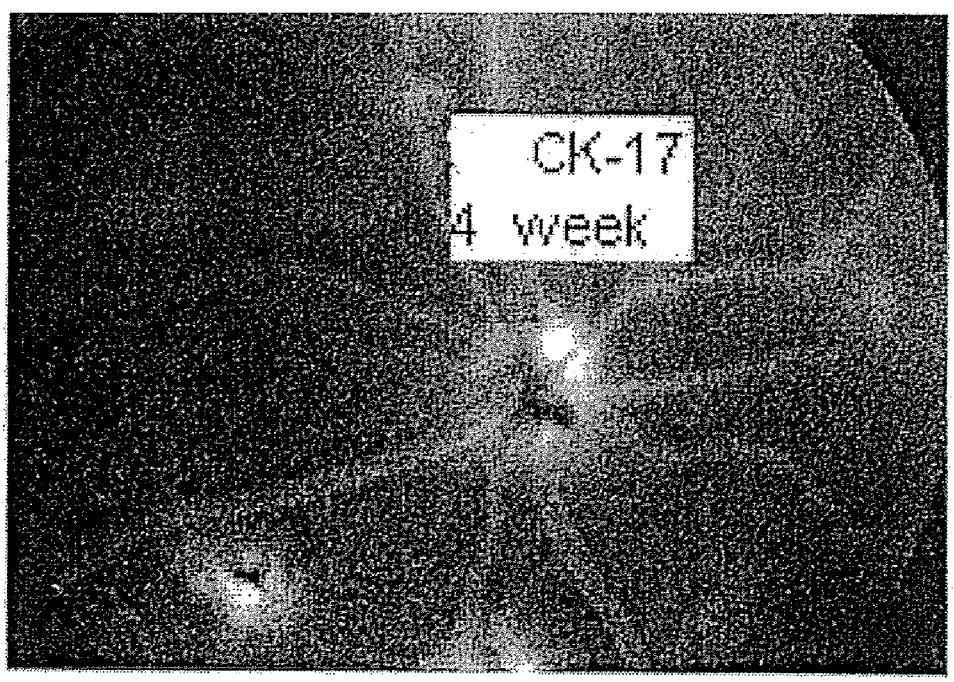
FIG. 5 is a fluorescein angiograph that shows the inhibition of CNV formation by intraperitonal administration of 30 mg/kg CK-17.
Figure 6:
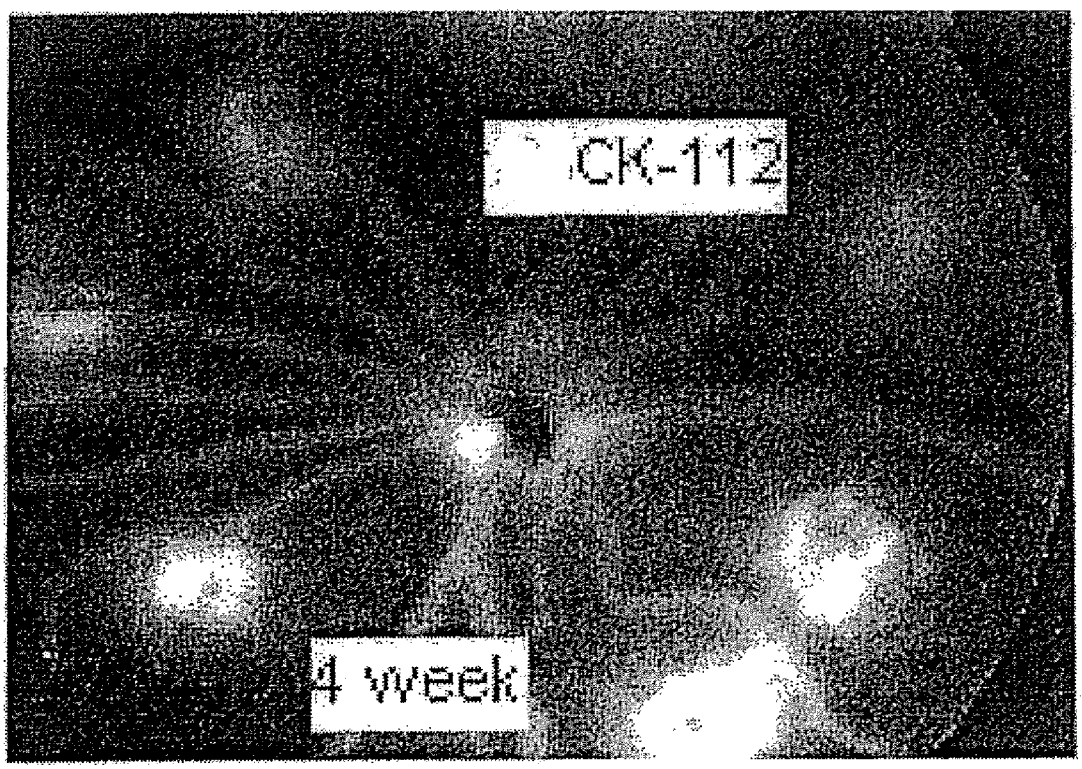
FIG. 6 is a fluorescein angiograph that shows the inhibition of CNV formation by intraperitonal administration of 10 mg/kg CK-112.
Figure 7:
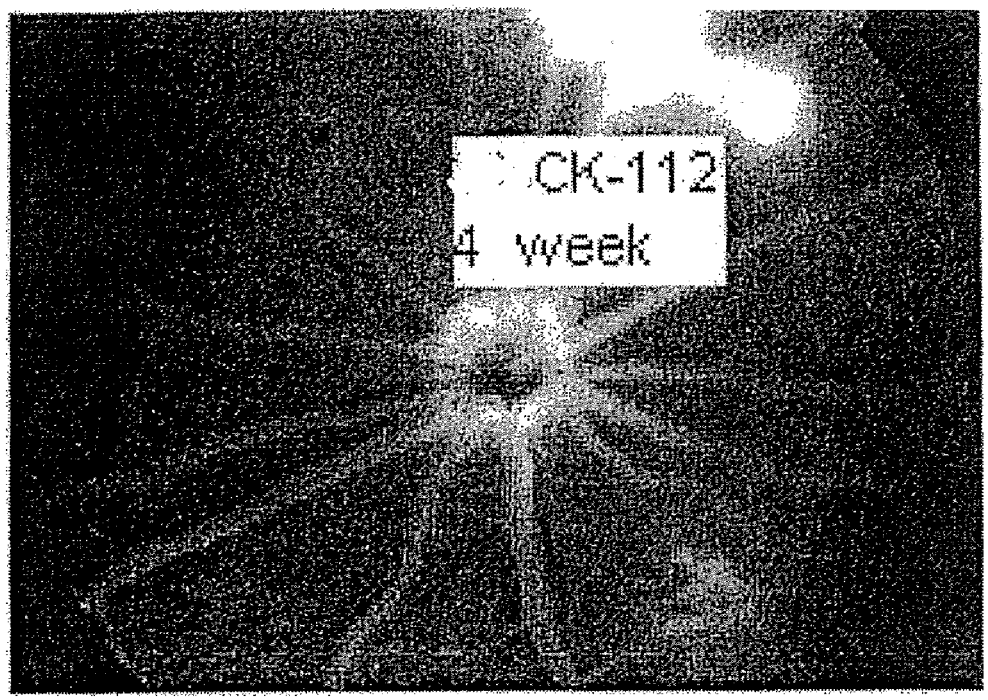
FIG. 7 is a fluorescein angiograph that shows the inhibition of CNV formation by intraperitonal administration of 30 mg/kg CK-112.
Figure 8:
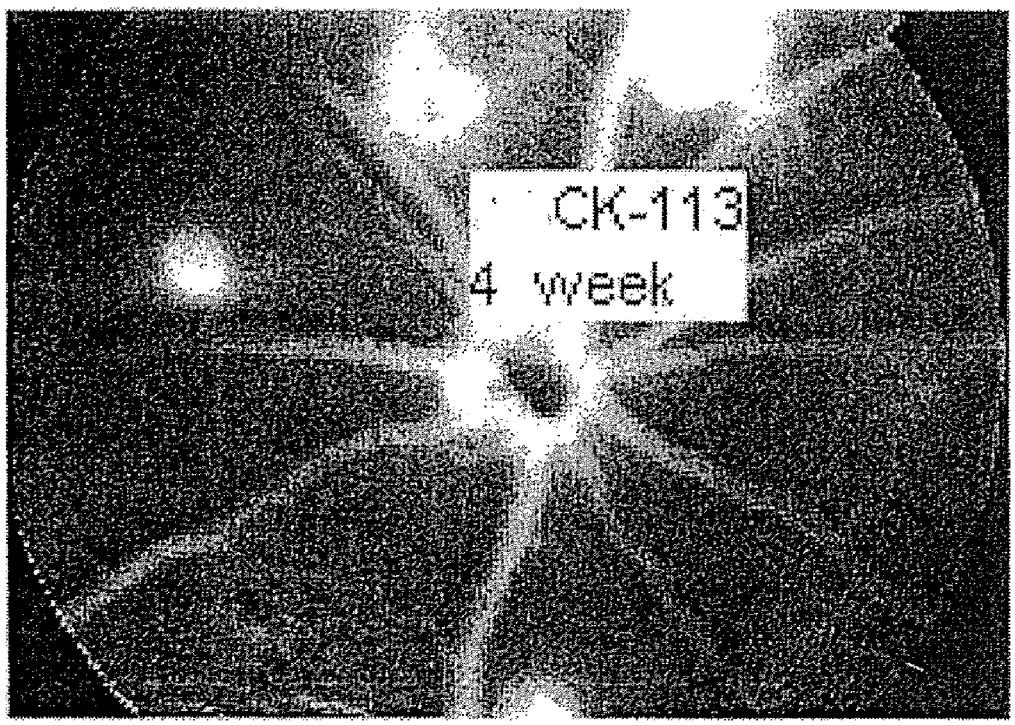
FIG. 8 is a fluorescein angiograph that shows the inhibition of CNV formation by intraperitonal administration of 30 mg/kg CK-113.

CK-17 at 30 mg/kg i.p. showed even better results than prednisolone at 3 mg/kg i.p. by inhibiting at least six out of eight CNV spots (FIG. 5). The results of CK-112 at 10 mg/kg i.p. were about the same as prednisolone at 3 mg/kg i.p. (FIGS. 4 and 6). When the dose of CK-112 was raised to 30 mg/kg i.p. the results were even better (FIG. 7) and were about the same as that of CK-17 at 30 mg/kg i.p. (FIG. 5). The effect of CK-113 at 30 mg/kg i.p. was similar to that of CK-112 at 10 mg/kg i.p. (FIGS. 7 and 8).

Figure 9:
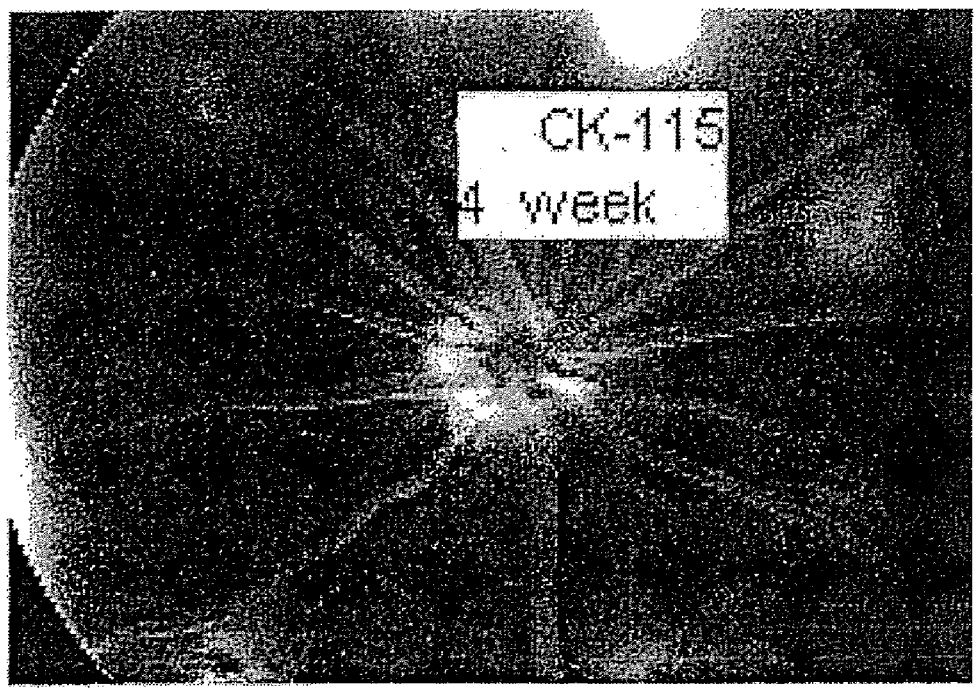
FIG. 9 is a fluorescein angiograph that shows the inhibition of CNV formation by intraperitonal administration of 10 mg/kg CK-115.
Figure 10:
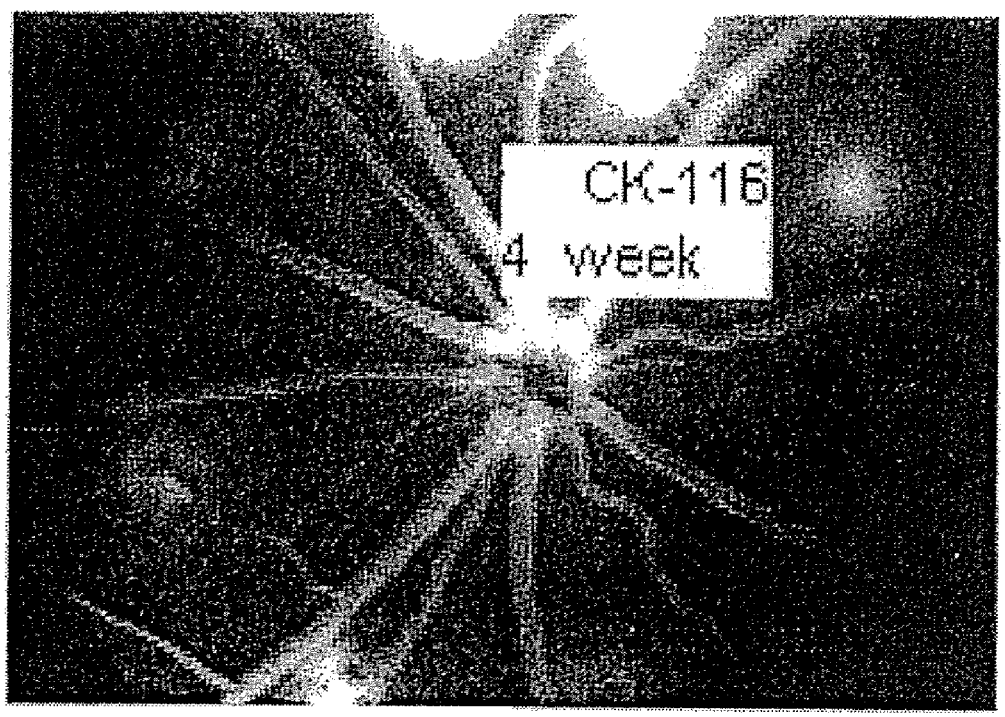
FIG. 10 is a fluorescein angiograph that shows the inhibition of CNV formation by intraperitonal administration of 10 mg/kg CK-116.
Figure 11:
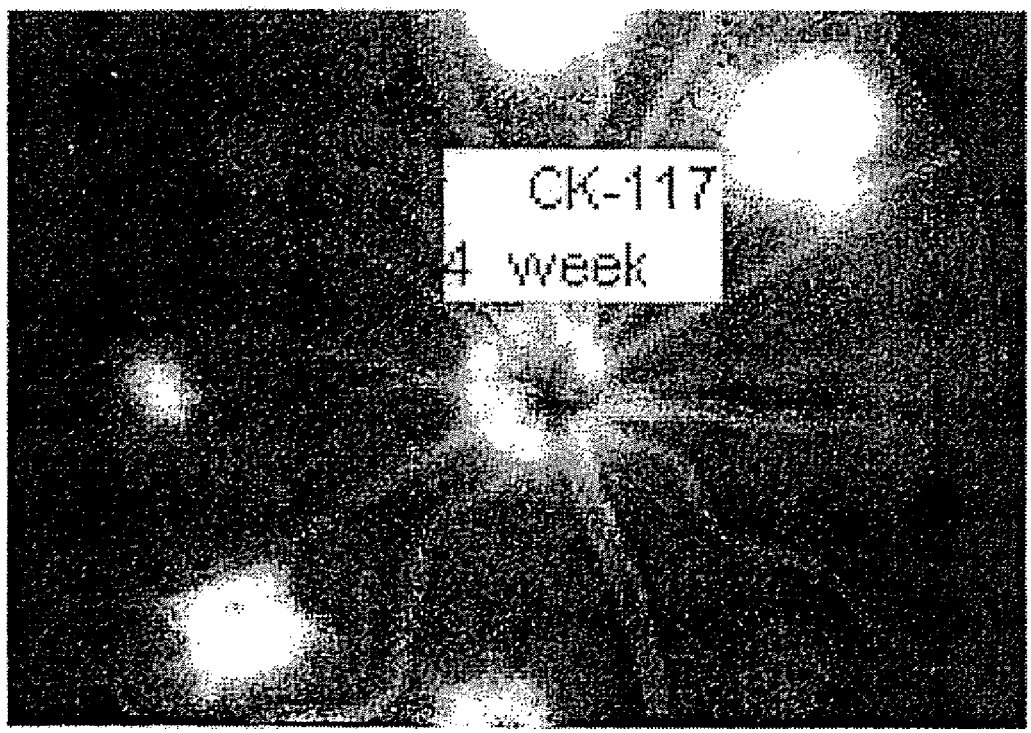
FIG. 11 is a fluorescein angiograph that shows the inhibition of CNV formation by intraperitonal administration of 10 mg/kg CK-117.
Figure 17:
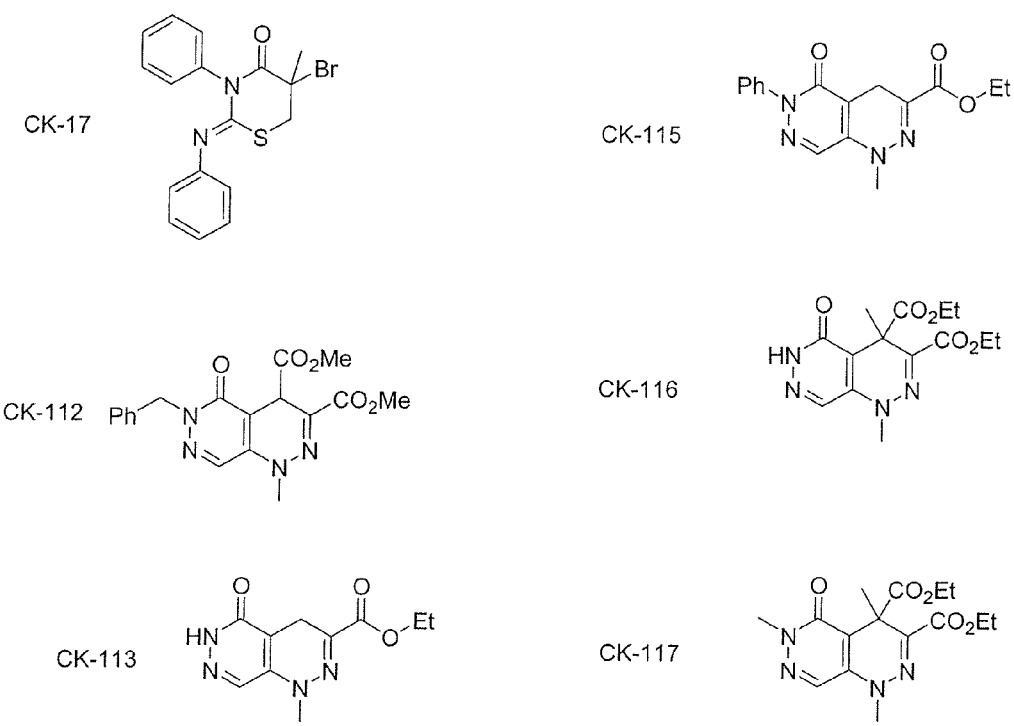
FIG. 17 shows the chemical structures of CK-17, CK-112, CK-113, CK-115, CK-116, and CK-117.
Figure 19:
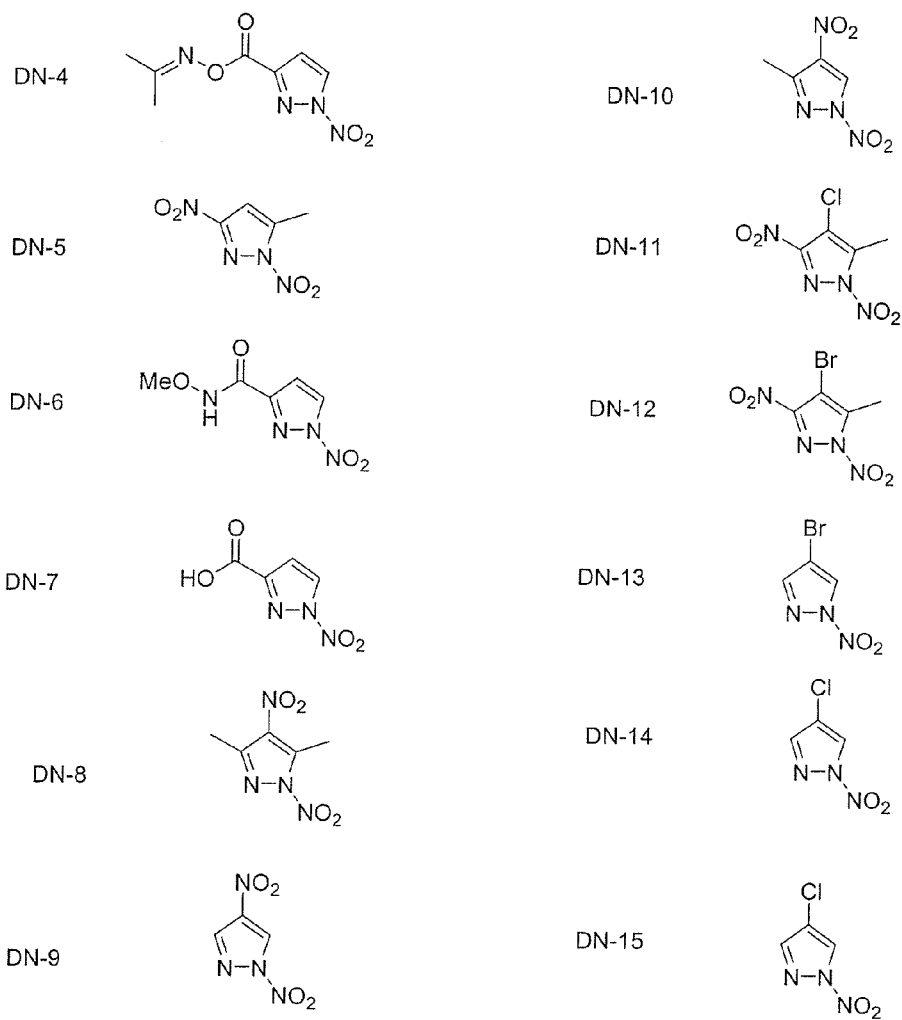
FIG. 19 shows the chemical structures of DN-4 through DN-15.
Figure 20:
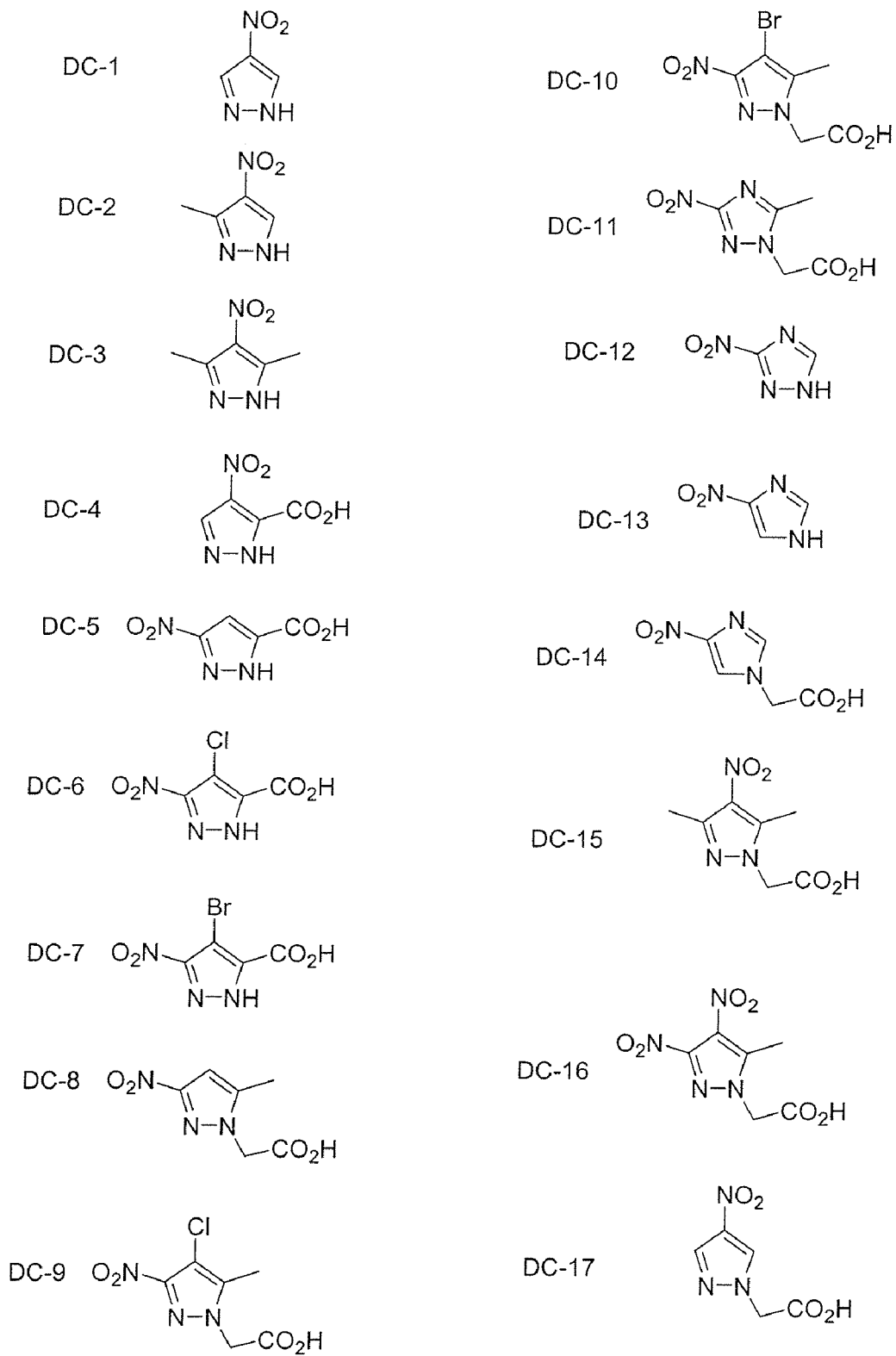
FIG. 20 shows the chemical structures of DC-1 through DC-17.

The effect of CK-115 at 10 mg/kg i.p. was quite impressive (FIG. 9). It inhibited markedly seven out of eight CNV spots. CK-116 at 10 mg/kg i.p. (FIG. 10) was similar to that of CK-112 at 10 mg/kg i.p. (FIG. 6) whereas CK-117 at 10 mg/kg i.p. was less efficacious (FIG. 11).

However, by raising the doses, the inhibitory action on CNV formation would be definitely improved, as long as the toxicities of these compounds remain at minimal level.

Experiments were done by using laser beam induced CNV through breaking down of Bruch's membrane. Prednisolone showed inhibition of CNV formation as expected. However, the toxicity of prednisolone and other steroidal anti-inflammatory agents provides concern for use in the clinics for the treatment of AMD. In this research, 3 mg/kg i.p. of prednisolone was the minimal dose required to produce inhibition of CNV formation. Yet with this dose level, some animals lost appetite and body weight. Higher doses even resulted in the death of animals. On the other hand, CK compounds were quite non-toxic. For example, CK-17 at 20 g/kg given orally did not cause any toxic response for at least 7 days observed whereas the effective dose to inhibit CNV formation was as low as 30 mg/kg i.p. Therefore, CK compounds can be used effectively and safely for the treatment of AMD through CNV formation inhibition.

It is under stood that the compounds can be extracted from natural sources, purchased commercially, or made by a variety of methods using processes as described in the book by Smith and March "March's Advance Organic Chemistry, 5$^{th}$ edition 2001." Flavonoids, such as naringenin, apigenin, quercetin, and flavon were commercially available. Hypotensive agents such as D-Timolol, hydralazine, and guanabenz were purchased commercially. Statistical Analysis. All data were analyzed with non-paired student's t-test. Significance between two means at a certain time point was considered significant when $P \leq 0.05$.

EXAMPLES

Example 1

Synthesis of Nitropyrazoles

It is under stood that the compounds can be made by a variety of methods using processes as described in the book by Smith and March "March's Advance Organic Chemistry, 5$^{th}$ edition 2001". DC-5, C-nitropyrazoles, were prepared using procedures described in Shevelev et al., Russ Chem Bull 44:1861-4 (1993), Kanishchev et al., Bull Acad Sci USSR Div Shem Sci 35:2191 (1986), Torf et al., J Gen Chem 32:1740-6 (1962). Compounds DN-4 through DN-15 were obtained by N-nitration of the corresponding pyrazoles. Compound DN-5 was synthesized according to the methods provided in Ugrak et al., Russ. Chem. Bull. 42:1555-1558, 1993. Compound DN-7 was synthesized according the methods provided in Dalinger et al., Russ. Chem. Bull. 36:1149-1153, 1997. Compounds DN-8, DN-10, DN-11, DN-12, DN-13, and DN-14 were synthesized according to the methods provided in Huttel Chem. Ber. Bd. 88:1586-1590 (1955) and Chem. Ber. 88:1577-85 (1955). DN-9 and DN-15 were synthesized according to the methods provided in Janssen el at, J. Org. Chem. 38:1777-1782 (1973). Compounds DN-4 and DN-6 were synthesized according to the methods provided in Xuan et al., J. Ocular Pharma. Thera. 17(6):505-515 (2001).

Example 2

Synthesis of Pyridazino[4,5-c]pyridazinones

Synthetic compounds including CK-17, CK101A, CK103A, CK 112, CK 113, CK 114, CK 115, CK 116, CK 119, CK 120, and CK 122 were synthesized according to the methods provided in Okawara, et al., Chem. Pharm. Bull. 31:507-512. (1983), Yamasaki et al., J. Chem. Soc. Perkin Trans. 1:991-996 (1991), Yamasaki et al., J. Heterocyclic Chem. 29:1313-1316 (1992), and Bo & Chiou Zhongguo Yao Li Xue Bao. 19(4):304-8 (1998). Other compounds such as flufenamin acid, indomethacin, ibuprofen, and NDGA (Nor-dihydroguaiaretic acid) and natural products, such as prednisolone, tetrandrine, quercetin, pulegone, friedelin, naringen and dihydrojasmon were purchased commercially. One prepares other derivatives according to Robins et al., Synthesis of some 7- and 5,7-substituted pyrazolo[4,3-d]pyrimidines. J Am Chem Soc 78:2418-22 (1956).

Example 3

Measurement of Choroidal Blood Flow in Ocular Hypertensive Rabbit Eyes

New Zealand white rabbits, weighing 2.5-3.0 kg, were anesthetized with 35 mg/kg ketamine and 5 mg/kg xylazine intramuscularly. Half of the initial dose was given hourly to maintain anesthesia. An ocular hypertensive model was created by raising the intraocular pressure of the left eye to 40 mmHg which reduced the ocular blood flow to approximately ⅓ of the normal values. The left ventricle was cannulated through the right carotid artery for the injection of microspheres, and the femoral artery was cannulated for blood sampling. One percent drug solution (50 µl) or vehicle (50 µl) was instilled topically to the left eye, and the ocular blood flow of the ocular hypertensive rabbits was measured with colored microspheres at 0, 30, 60, and 120 min thereafter. At each time point, 2 million microspheres in 0.2 mL were injected as a reference, and blood samples were taken from the femoral artery for exactly one minute following injection of the microspheres. The blood sample was collected in a heparinized tube, and the volume was recorded. The rabbits were euthanized with an injection of 100 mg/kg pentobarbital sodium after the last blood sampling. The left eyes were enucleated and dissected into the retina, choroid, iris, and ciliary body. The tissue samples were weighed.

The details of sample processing and microsphere counting were provided by E-Z Trac (Los Angeles, Calif.). In brief, Hemolysis Reagent was added to the microfuge tubes with the blood sample, then vortexed and centrifuged for 30 min at 6000 rpm. The supernatant was removed, and the Tissue/Blood Digest Reagents I and II were added. The tubes were capped, vortexed, and centrifuged for 30 min again. The supernatant was removed, and the Counting Reagent was added, then vortexed, and centrifuged for 15 min at the same revolutions as above. The supernatant was removed, and the microspheres were resuspended in a precise volume of the Counting Reagent. The number of microspheres was counted with a hemocytometer.

The Tissue/Blood Digest Reagent I was added to the microfuge tubes with the tissue samples, sealed, and heated at 95° C. for 15 min. The tubes were vortexed for 30 sec, reheated and revortexed until all tissue samples were dissolved. The Tissue/Blood Digest Reagent II was added while the tissue samples were still hot, then the tubes were capped, vortexed, and centrifuged for 30 min. The protocol, thereafter, was the same as that used to process the blood sample, and the microspheres were counted.

The blood flow of each tissue at a certain time point was calculated from the following equation:

$$Qm=(Cm \times Qr)/Cr$$

Where Qm is the blood flow of a tissue in terms of μL/min/mg, Cm is the microsphere count per mg of tissue, Qr is the flow rate of blood sample in terms of μL/min, and Cr is the total microsphere count in the referenced blood sample.

Example 4

Measurement of Retinal Function Recovery After Ischemic Insult in Rat Eyes

Electroretinograms (ERGs) were determined to provide assessment of the retinal function prior to and following ischemic insult. ERGs were recorded by means of Ag/AgCl electrodes placed in contact with the cornea. One stainless steel needle was inserted subcutaneously between the two eyes as a reference electrode, and another needle was inserted subcutaneously to the neck as a ground electrode. A photostimulator (Grass PS22 Flash) was used to produce flashes of light five inches from the eye, and the ERG potentials were recorded with a polygraph system. The ERG machine was purchased from LKC Technologies, Inc. (Gaithersburg, Md.). A single (10 msec duration), white light stimuli was used to elicit ERG a- and b-waves. Peak b-wave amplitudes were measured from the trough of a-wave to the peak of b-wave.

Dark-adapted, female Long-Evans rats (200-250 g) were anesthetized with 35 mg/kg ketamine plus 5 mg/kg xylazine intramuscularly. Half of the initial dose was given thereafter at one-hour intervals to maintain adequate anesthesia. The pupils were dilated with 1% tropicamide plus 10% phenylephrine (50 μl) for ERG experiments. Retinal ischemia was produced by occlusion of the central retina and posterior ciliary arteries by means of a ligature placed around the optic nerve and the posterior ciliary artery. The ligature was then tightly drawn for 30 min to occlude the retinal vessels. Retinal ischemia was confirmed by the extinction of the ERG waves. After 30 min of retinal ischemia, ligature was released and the retinal arteries allowed to reperfuse. ERGs were then measured at 0, 30, 60, 90, 120, 180, and 240 min thereafter. Drugs and vehicles were administered intraperitoneally. These drugs were administered immediately prior to occlusion of the central retinal arteries.

Example 5

Measurement of CNV Formation in Rat Eyes after Induction of Choroidal Neovascularization Brown-Norway rats, weighing 200-250 g, were anesthetized with ketamine 35 mg/kg and xylazine 5 mg/kg. Pupils were dilated with a topical application of 1% tropicamide (Bausch & Lomb; Tampa, Fla.) and 2.5% Neo-Synephrine (Sanofi-Synthelabo Inc.; NY). CNV was experimentally induced with a double frequency Nd:YAG laser (Laserex LP3532; Ellex Medical PTY. LTD., Australia) to disrupt Bruch's membrane. The laser wavelength was 532 nm, and spot size was 100 μm. Power delivered ranged from 130 to 150 mW, applied for 0.1 sec. Typically, eight lesions were induced in both eyes of each animal. On occasion, the inducing laser burst created an extensive subretinal and/or vitreous hemorrhage, and these spots were excluded from any further treatment or analysis. Other lesions in the same eye were included in the study if the subretinal hemorrhage did not extend to within approximately 1 mm of the lesion. The presence of CNV was confirmed at 2 weeks after laser induction by fluorescein angiography. Each laser lesion was evaluated as follows: Leaking (++): increase in size of hyperfluorescence over time; Non-leaking (+): only staining without increase in size of hyperfluorescence; Non-evaluation (−): fluorescein angiography could not evaluate the lesion due to masking by the overlying hemorrhage.

Fluorescein Angiography. Fluorescein angiography was performed in anesthetized animals with dilated pupils using a Digital Fundus Camera (TRC-50 EX: Topcon, Japan) and standard fluorescein filter 0.3 ml of 10% fluorescein (Sigma-Aldrich Inc.; St. Louis, Mo.) was injected intravenously via hypoglossal vein. After injection, the camera alternated between both eyes taking images for 10 minutes. Fluorescein angiography was performed in all rats at 2 and 4 weeks following simultaneous laser induction of CNV and drug-vehicle injection.

In vivo Evaluation: All rats were examined weekly after laser induction of CNV and drug/vehicle injection up to the time of sacrifice. The examination was performed by slit lamp (SL-3E; Topcon, Japan) to evaluate the anterior segment and by indirect ophthalmoscope (Omega 200; Heine, Germany) using a 20 D lens to evaluate the retina and vitreous.

Example 7

Interleukin-1 Induced Uveitis

Female Sprague-Dawley rats, weighing 250-300 g, were anesthetized with 35 mg/kg ketamine and 5 mg/kg xylazine intramuscularly. Ten μl of 1.0 ng of IL-1α were injected intravitreously with 30-gauge needle, and the rats were allowed to recover from the anesthesia. CK-compounds, at doses of 3 mg/kg or 10 mg/kg, were injected intraperitoneally (i.p) at time 0, 4, and 10 hours after the IL-1α injection. The inflammation was measured 12 hours after IL-1α injection. The rats were anesthetized again as described previously, and FD-70 solution (1.4 ml/kg) was injected intravenously through the hypoglossal vein. Scanning of the eyes was conducted with a fluorophotometer (Fluorotron Master, Coherent Corp., Palo Alto, Calif.). Measurements were carried out at 0, 30, 60, 90, 120, 180, 240, 300, and 360 min after FD-70 injection. The peak level of FD-70 in the eye was reached at 300 min after the FD-70 injection.

Example 8

Trabeculectomy Induced Inflammation

Adult Dutch Belted rabbits were purchased commercially and were specific pathogen free for Pasteurellosis. Rabbits were housed in individual cages and kept on twelve-hour, light-dark cycle. The room temperature was maintained at 25° C. and the relative humidity was 50%. Rabbits were given access to rabbit chow (Harland, Houston, Tex.) and water ad libitum. Rabbits were fasted for twelve hours before induction of anesthesia.

The animals were predosed with an antimuscarinic and sedative. The rabbit was induced with ketamine/xylazine, intuvated and then maintained anesthetized with isoflurane. Buprenorphine and pancuronium were also used for a balanced anesthetic regimen. Ten mg/kg buprenorphine was administered every 12 hours for three days for analgesia post operatively.

A glaucoma filtration operation with partial thickness scleral flap was completed using an operating microscope and a strict aseptic technique. A limbus based conjunctival flap was created. Then, approximately one millimeter temporal to the superior rectus, a partial thickness miniflap was formed in the sclera. The flap dimensions were three millimeters at the limbus, two millimeters on the sides and at the base. At the surgical limbus a 2.5 millimeter sclerostomy was performed using a razor blade chip. A Kelly Descement punch (Storz, St. Louis, Mo.) was then used to complete the sclerostomy. A peripheral iridectomy was then performed. The iris was reposited with a balanced salt solution flush and gentle corneal massage. The scleral flap was then sutured closed with a single 10-0 micorsurgical nylon suture and fixed with an overlying square knot. The conjunctiva and the tenons incision were closed with a running 10-0 suture. Immediately upon water-tight closure of the conjunctiva, a filtration bleb could be noted. The same procedure was done on the contralateral eye.

In vivo Evaluation. All rats were examined weekly after laser induction of CNV and drug/vehicle injection up to the time of sacrifice. The examination was performed by slit lamp (SL-3E; Topcon, Japan) to evaluate the anterior segment and by indirect ophthalmoscope (Omega 200; Heine, Germany) using a 20 D lens to evaluate the retina and vitreous.

Prior to surgery, the rabbits were randomly assigned to one of seven groups 1) vehicle control subtenons injection (STI), 2) prednisolone eye drops, 3) no drug 4) methylprednisolone STI, 5) CK-17 STI, 6) CK-101A STI, and 7) CK-102 STI. The animals in the eye drops group received two drops in each eye three times per day. The eye drops 50 μl treatment began the day before surgery and continued until failure of the fistula. The control for the eye drops group was "no drug" because the formulation of the eye drops is patented and therefore, a vehicle control could not be prepared. If the animal was in subtenons treatment group, then 10 mg of the drug was given by subtenons injection while the animal was still under general anesthesia. If the animal was in the vehicle control group, a volume of the vehicle was given equal to that given in the treatment groups. Finally, 20 mg gentamicin was given subconjunctivally for prophylaxis of microbial infection.

The eyes were preanesthetized with one to two drops of tetracaine instilled into both eyes and the intraocular pressure was measured by applanation pneumotonography (Alcon, Ft. Worth, Tex.). Preoperative measurements were recorded the day before surgery. Postoperative measurements were recorded every other day. Failure of the filtration fistula was defined as the point where IOP returned to preoperative values or the same value was recorded for three consecutive readings. The presence or absence of the filtration bleb was also recorded every other day. On the days when IOP was not measured, biomicroscope examinations were conducted and the inflammation was scored using the system previously defined by Miyano & Chiou, Ophthalmic. Res. 16:256-263 (1984). For biomicroscope examination, the rabbit was anesthetized with 1 mg/kg acepromazine IM. Inflammation scores were calculated and recorded. At the conclusion of the experiment the animals were euthanized with an overdose (100 mg/kg) of pentobarbital sodium.

Example 9

Carrageenin-induced Inflammation

Forty female Sprague Dowley rats weighing 164±16 g were used for the experiments. The test and control groups were assigned randomly. Carrageenin (0.1 mL of 1% solution) was injected into the plantar surface of the rat hind paw to induce inflammation. Ten minutes before carrageenin injection, 8 mL of water administered ig. CK-17, and aspirin were grounded with Tween 80 and then suspended into distilled water. CK-17, or aspirin were injected ip 3 times at time 0, 8, and 16 h before the injection of carrageenin. The changes in volume of the inflamed edematous foot were measured by the volume of water displaced and recorded at 0, 0.5, 1, 2, 4, and 6 h after the carrageenin injection.

$LD_{50}$ determination: For each dose, 20 mice of either sex, weighing 18-20 g were used to determined the $LD_{50}$ according to the method of Litchfield & Wilcoxon, J. Pharmacol. Exp. Ther. 96:99-113 (1949). Animals were housed in an animal room at 25° C. and 70% relative humidity. The light cycle was set for 12 h light and 12 h darkness. CK-17 was grounded with Tween 80 and then suspended in 1% CMC (carboxymethyl cellulose). The suspension was administered ig at 20 g/kg and the animals were observed for 7 d.

Example 10

Eye Irritation Test

Draize test, Draize et al., J. Pharmacol. Exp. Ther. 82:377-90 (1944), was followed for the determination of eye irritation. Before the Draize test, it was already known that CK-17 did not produce skin irritation in guinea pigs. So, Draize test was used to show the safety rather than the toxicity of drugs in the rabbit eyes in this experiment. Six New Zealand albino rabbits of either sex, weighing 2-2.5 kg were used in each group. Animals were housed individually in cages at 25° C. and 70% relative humidity. The light cycle was maintained at 12 h light and 12 h dark for 7 d after the instillation of CK-17 or vehicle as controls.

CK-17 (0.1%) was suspended in 6% dimethylsulfoxide (DMSO), 6% PEG 400, 10% Tween 80, and 78% saline. Fifty microliters of the test compound was instilled into the cul de sac of the right eye as treated and the vehicle to the left eye as control. The eye lids were gently held together for 10 s to prevent the loss of the materials. Animals showing eye irritation, ocular defects or pre-existing corneal injuries were not used for the experiment. The eyes were examined with ophthalmoscopy at 0, 1, 3, 5, 7, and 24 h, and 2 d, 3 d, 5 d, and 7 d after the eye drop instillation. The scores of the Irritation Table were recorded and calculated.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of treating macular degeneration, comprising:
   topically administering a composition comprising hydralazine or a salt thereof to at least one eye of a subject diagnosed with age-related dry macular degeneration.

2. The method of claim 1, wherein said subject is a human.

3. The method of claim 1, wherein said salt is a hydrochloride salt, a hydrochlorothiazide salt or an isosorbide dinitrate salt.

4. The method of claim 1, wherein said composition is a liquid solution.

5. The method of claim 1, wherein said administering comprises topically administering the composition to both eyes of the subject.

6. A method of treatment, comprising:
   topically administering a composition comprising hydralazine or a salt thereof to at least one eye of a subject diagnosed with age-related dry macular degeneration and at risk for choroidal neovascularization.

* * * * *